(12) United States Patent
Ozaki et al.

(10) Patent No.: US 12,209,185 B2
(45) Date of Patent: Jan. 28, 2025

(54) COLOR MATERIAL COMPOUND

(71) Applicants: DIC Corporation, Tokyo (JP); HAYASHIBARA CO., LTD., Okayama (JP)

(72) Inventors: Yusuke Ozaki, Sakura (JP); Ayaka Yamaji, Sakura (JP); Takako Tanaka, Sakura (JP); Daisuke Kuraoka, Okayama (JP); Noriaki Neki, Okayama (JP); Hiroshi Nagaike, Okayama (JP)

(73) Assignees: DIC CORPORATION, Tokyo (JP); NAGASE VIITA CO., LTD., Okayama (JP)

(*) Notice: Subject to any disclaimer, the term of this patent is extended or adjusted under 35 U.S.C. 154(b) by 615 days.

(21) Appl. No.: 17/628,312

(22) PCT Filed: Jun. 23, 2020

(86) PCT No.: PCT/JP2020/024570
§ 371 (c)(1),
(2) Date: Jan. 19, 2022

(87) PCT Pub. No.: WO2021/014862
PCT Pub. Date: Jan. 28, 2021

(65) Prior Publication Data
US 2022/0259434 A1   Aug. 18, 2022

(30) Foreign Application Priority Data
Jul. 25, 2019  (JP) .................. 2019-137231

(51) Int. Cl.
| | | |
|---|---|---|
| C07F 11/00 | (2006.01) | |
| C09B 23/04 | (2006.01) | |
| C09B 23/08 | (2006.01) | |
| G02B 1/04 | (2006.01) | |
| H10K 85/60 | (2023.01) | |
| G02B 5/22 | (2006.01) | |

(52) U.S. Cl.
CPC ............ *C09B 23/08* (2013.01); *C07F 11/005* (2013.01); *C09B 23/04* (2013.01); *C09B 23/083* (2013.01); *G02B 1/04* (2013.01); *H10K 85/6572* (2023.02); *G02B 5/22* (2013.01)

(58) Field of Classification Search
CPC .................................................. C07F 11/005
See application file for complete search history.

(56) References Cited

U.S. PATENT DOCUMENTS 4,785,088 A   11/1988 Flohr et al.
4,849,306 A   7/1989 Raue et al.

FOREIGN PATENT DOCUMENTS

| CN | 106892855 A | 6/2017 |
|---|---|---|
| JP | 62-554 A | 1/1987 |
| JP | 63-231359 A | 9/1988 |
| JP | 6-320869 A | 11/1994 |
| JP | 10-81068 A | 3/1998 |
| JP | 11-129624 A | 5/1999 |
| JP | 2014-19771 A | 2/2014 |
| JP | 2015-48433 A | 3/2015 |
| JP | 2015-183134 A | 10/2015 |
| JP | 2017-114955 A | 6/2017 |
| WO | 2017/145627 A1 | 8/2017 |

OTHER PUBLICATIONS

A machine generated English translation of JP 06-320869 A, 1994 (Year: 1994).*
Office Action dated May 31, 2024, issued in counterpart CN application No. 202080052318.8, with partial English translation. (9 pages).
Wang, Jingyi, "Manufacturing Technology of Color Filters", Mircofabrication technology, Dec. 1994. (7 pages).
International Search Report dated Sep. 15, 2020, issued in counterpart International Application No. PCT/JP2020/024570, w/English translation (6 pages).

* cited by examiner

*Primary Examiner* — Laura L Stockton
(74) *Attorney, Agent, or Firm* — WHDA, LLP

(57) ABSTRACT

The present invention relates to a compound represented by general formula (I) (in the formula (I), X represents a methyl group or a halogen atom; $R^1$ to $R^{14}$ each independently represent a hydrogen atom, a halogen atom, a cyano group, an optionally substituted alkyl group having 1 to 8 carbon atoms, or an optionally substituted aromatic hydrocarbon group having 6 to 12 carbon atoms; $B^{m-}$ represents a polyoxometalate anion; m represents an integer of 1 to 20; n represents an integer of 1 to 20, provided that n is determined such that the charge of the whole formula (I) becomes zero).

[Chem. 1]

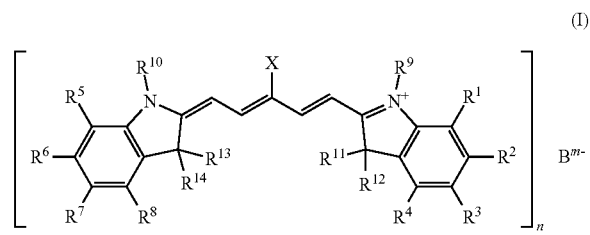

5 Claims, 5 Drawing Sheets

COLOR MATERIAL COMPOUND

TECHNICAL FIELD

The present invention relates to a compound, specifically, a new compound suitable as a color material compound for forming a blue pixel portion of a color filter.

The application claims the benefit of Japanese Patent Application No. 2019-137231, filed Jul. 25, 2019, which is hereby incorporated by reference herein in its entirety.

BACKGROUND ART

The color filters of liquid crystal displays and so on include a red pixel portion (R), a green pixel portion (G), and a blue pixel portion (B). These pixel portions each have a structure in which a thin film of a synthetic resin dispersing an organic pigment therein is disposed on a substrate, and as the organic pigment, organic pigments of red, green, and blue are mainly used.

As a blue organic pigment for forming a blue pixel portion among these pixel portions, in general, an ε-type copper phthalocyanine pigment (C.I. Pigment Blue 15:6) is used, and a small amount of a dioxazine violet pigment (C.I. Pigment Violet 23), which is a violet organic pigment, or a violet dye is used in combination as needed for toning.

CITATION LIST

Patent Literature

PTL 1: Japanese Unexamined Patent Application Publication No. 2014-019771
PTL 2: Japanese Unexamined Patent Application Publication No. 2015-183134
PTL 3: Japanese Unexamined Patent Application Publication No. 2017-114955

SUMMARY OF INVENTION

Technical Problem

The organic pigment for producing a color filter is required to have characteristics completely different from those in usual general use, specifically, making the display screen of a liquid crystal display or the like clearer (increase in contrast) or likewise making the display screen brighter (increase in luminance). In particular, the organic pigment that is used in a blue pixel portion (B) is especially required to have increased luminance.

In order to correspond to such an increase in luminance, it has long been studied to use a dye having luminance more excellent than that of ε-type copper phthalocyanine pigment in the blue pixel portion of a color filter.

However, dyes have a problem of insufficient resistance to heat of 200° C. or more that is required in manufacturing step of a color filter.

As a countermeasure, a method of chelating a dye is regarded as promising, but nothing has beer, found that is superior to ε-type copper phthalocyanine pigment in luminance (e.g., PTLs 1 to 3).

Accordingly, it is an object of the present invention to provide a color material compound that can be suitably used for forming a blue pixel portion of a color filter.

Solution to Problem

The present invention encompasses the following aspects:
[1] A compound represented by the following formula (I):

[Chem. 1]

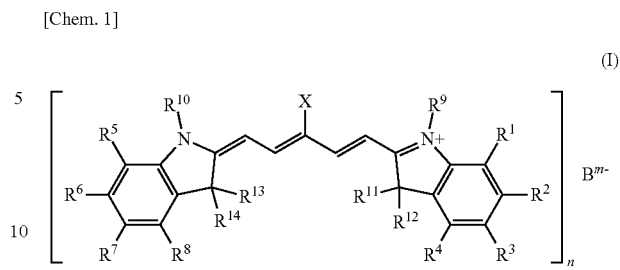

(In the formula (I),
X represents a methyl group or a halogen atom;
$R^1$ to $R^{14}$ each independently represent a hydrogen atom, a halogen atom, a cyano group, a nitro group, an optionally N-alkylated amino group or ammonium group, a hydroxy group, an allyloxy group, an alkoxy group, a sulfo group, an optionally N-alkylated sulfamoyl group, a carboxyl, group, an ester group, an optionally N-alkylated amide group, an optionally substituted hydrocarbon group having 1 to 12 carbon atoms, an optionally substituted aromatic hydrocarbon group having 6 to 12 carbon atoms, or an optionally substituted heterocyclic group having 3 to 12 carbon atoms, and adjacent two selected from $R^1$ to $R^4$, adjacent two selected from $R^5$ to $R^8$, $R^{11}$ and $R^{12}$, or $R^{13}$ and $R^{14}$ may be bonded to each other to form a ring;
$B^{m-}$ represents a polyoxcmetalate anion;
m represents an integer of 1 to 20; and
n represents an integer of 1 to 20,
provided that n is determined such that the charge of the whole formula (I) becomes zero);
[2] The compound according to the above [1], wherein in the formula (I), X is a methyl group, a chlorine atom, or a bromine atom;
[3] The compound according to the above [1], wherein in the formula (I), $B^{m-}$ is a polyoxometalate anion at least including tungsten;
[4] The compound according to the above [3], wherein in the formula (I), $B^{m-}$ is $(PW_{12}O_{40})^{3-}$, $(PM_oW_{11}O_{40})^{3-}$, $(SiW_{12}O_{40})^{4-}$, or $(SiMoW_{11}O_{40})^{4-}$; and
[5] The compound according to the above [3] or [4], wherein in the formula (I), X is a methyl group, a chlorine atom, or a bromine atom.

Advantageous Effects of Invention

According to the present invention, it is possible to provide a color material compound that can be suitably used for forming a blue pixel portion of a color filter.

Figure 1:
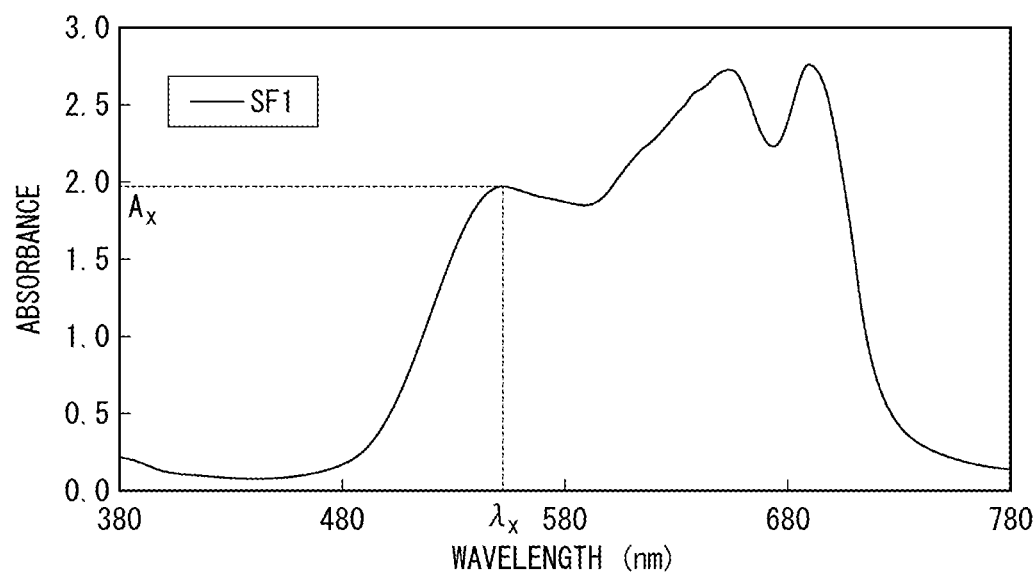
FIG. 1 is an absorption spectrum of a colored film of a glass substrate (SF1) for single color evaluation.

DESCRIPTION OF EMBODIMENTS (Compound Represented by General Formula (I))

The compound of the present invention is represented by the general formula (I).

[Chem. 2]

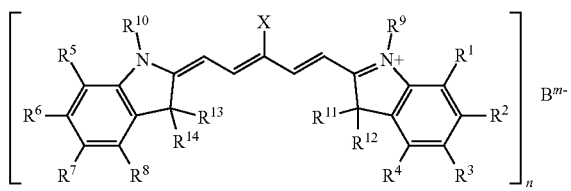

(In the formula (I),

X represents a methyl group or a halogen atom;

$R^1$ to $R^{14}$ each independently represent a hydrogen atom, a halogen atom, a cyano group, a nitro group, an optionally N-alkylated amino group or ammonium group, a hydroxy group, an allyloxy group, an alkoxy group, a sulfo group, an optionally N-alkylated sulfamoyl group, a carboxyl, group, an ester group, an optionally N-alkylated amide group, an optionally substituted hydrocarbon group having 1 to 12 carbon atoms, an optionally substituted aromatic hydrocarbon group having 6 to 12 carbon atoms, or an optionally substituted heterocyclic group having 3 to 12 carbon atoms, and adjacent two selected from $R^1$ to $R^4$, adjacent two selected from $R^5$ to $R^8$, $R^{11}$ and $R^{12}$, or $R^{13}$ and $R^{14}$ may be bonded to each other to form a ring;

$B^{m-}$ represents a polyoxcmetalate anion;

m represents an integer of 1 to 20; and n represents an integer of 1 to 20, provided that n is determined such that the charge of the whole formula (I) becomes zero.)

X represents a methyl group or a halogen atom. Examples of the halogen atom represented by X include a fluorine atom, a chlorine atom, a bromine atom, and an iodine atom. X is preferably a methyl group, a chlorine atom, or a bromine atom.

$R^1$ to $R^{14}$ each independently represent a hydrogen atom, a halogen atom, a cyano group, a nitro group, an optionally N-alkylated amino group or ammonium group, a hydroxy group, an allyloxy group, an alkoxy group, a sulfo group, an optionally N-alkylated sulfamoyl group, a carboxyl group, an ester group, an optionally N-alkylated amide group, an optionally substituted hydrocarbon group having 1 to 12 carbon atoms, an optionally substituted aromatic hydrocarbon group having 6 to 12 carbon atoms, or an optionally substituted heterocyclic group having 3 to 12 carbon atoms, and adjacent two selected from $R^1$ to $R^4$, adjacent two selected from $R^5$ to $R^8$, $R^{11}$ and $R^{12}$, or $R^{13}$ and $R^{14}$ may be bonded to each other to form a ring.

Examples of the halogen atom represented by $R^1$ to $R^{14}$ include a fluorine atom, a chlorine atom, a bromine atom, and an iodine atom.

Examples of the optionally N-alkylated amino group or ammonium group represented by $R^1$ to $R^{14}$ include an —$NH_2$ group, an —$NHR^{15}$ group, an —$NR^{17}R^{16}$ group, and an —$(NR^{18}R^{19}R^{20})^+$ group.

Examples of the alkoxy group represented by $R^1$ to $R^{14}$ include a methoxy group, an ethoxy group, a propoxy group, an isopropoxy group, a butoxy group, an isobutoxy group, a sec-butoxy group, a tert-butoxy group, and a pentyloxy group.

Examples of the allyloxy group represented by $R^1$ to $R^{14}$ include a phenoxy group and a naphthoxy group.

Examples of the optionally N-alkylated sulfamoyl group represented by $R^1$ to $R^{14}$ include an —$SO_2NH_2$ group, an —$SO_2NHR^{21}$ group, and an —$SO_2NR^{22}R^{23}$ group.

Examples of the ester group represented by $R^1$ to $R^{14}$ include a —$CO_2R^{24}$ group and an —$OCOR^{25}$ group.

Examples of the optionally N-alkylated amide group represented by $R^1$ to $R^{14}$ include a —$CONHR^{26}$ group and an —$NHCOR^{27}$ group.

Examples of the optionally substituted hydrocarbon group having 1 to 12 carbon atoms represented by $R^1$ to $R^{14}$ include linear saturated hydrocarbon groups, such as a methyl group, an ethyl group, a 1-propyl group, a 1-butyl group, a 1-pentyl group, a 1-hexyl group, a 1-heptyl group, and a 1-octyl group; branched saturated hydrocarbon groups, such as a 2-propyl group, a 2-butyl group, a 2-methyl-1-propyl group, a 1,1-dimethylethyl group, a 2-pentyl group, a 2-hexyl group, and a 2-ethyl-hexyl group; monocyclic hydrocarbon groups, such as a cyclopentyl group, a cyclohexyl group, a cyclopentenyl group, a cyclopentadienyl group, and a cyclohexenyl group; cyclic hydrocarbon groups with multiple ring structures, such as a dicyclopentanyl group, a dicyclepentenyl group, an isobornyl group, and an adamantyl group; hydrocarbon groups having a hydroxy group, such as a hydroxymethyl group and a 2-hydroxyethyl group; hydrocarbon groups having an amino group or an ammonium group, such as an aminomethyl group, an N-methyl-aminomethyl group, an N,N-dimethyl-aminomethyl group, an N,N,N-trimethyl-methanaminium group, a 2-aminoethyl group, a 2-(methylamino)ethyl group, a 1-(methylamino)ethyl group, a 2-(dimethylamino)ethyl group, a 1-(dimethylamino)ethyl group, and an N,N,N-trimethyl-2-ethanaminium group; hydrocarbon groups having a carboxyl group, such as a carhoxymethyl group, a carboxyethyl group, and a carboxylpropyl group; hydrocarbon groups having an aromatic substituent, such as a benzyl group; halogen-containing hydrocarbon groups, such as a fluoromethyl group, a difluoromethyl group, a trifluoromethyl group, a 2,2,2-trifluoroethyl group, a perfluoroethyl group, a 3,3,3-trifluoropropyl group, a 3,3,4,4,4-pentafluorobutyl group, a chioromethyl group, a chloroethyl group, a chloropropyl group, and a chlorobutyl group; and hydrocarbon groups having an ether bond, such as a methoxymethyl group, an ethoxymethyl group, a methoxyethyl group, and an ethoxymethyl group.

Examples of the optionally substituted aromatic hydrocarbon group having 6 to 12 carbon atoms represented by $R^1$ to $R^{14}$ include unsaturated aromatic hydrocarbon groups, such as a phenyl group, a 1-naphthyl group, and a 2-naphthyl group; alkyl-substituted aromatic hydrocarbon groups, such as a 2-methylphenyl group, a 3-methylphenyl group, a 4-methylphenyl group, a 2,4-dimethylphenyl group, a 2,4,6-trimethylphenyl group, a 3,5-dimethylphenyl group, and a cumenyl group; substituted aromatic hydrocarbon groups substituted with various functional groups, such as a 4-chlorophenyl group, a 4-methoxyphenyl group, a 4-aminophenyl group, a 4-hydroxyphenyl group, a 4-nitrophenyl group, a 4-carboxylphenyl group, and a 4-sulfophenyl group.

Examples of the optionally substituted heterocyclic group having 3 to 12 carbon atoms represented by $R^1$ to $R^{14}$ include a pyrrole ring, a furan ring, a thiophene ring, a pyridine ring, an imidazole ring, a pyrazole ring, an oxazole ring, a thiazole ring, an indole ring, an isoindole ring, a quinoline ring, and an isoquinoline ring.

The proton of the carboxyl group or the sulfo group included in the structure represented by $R^1$ to $R^{14}$ may be substituted with a metal ion, such as Na, or an organic cation, such as ammonium.

At least one of methylene groups (—$CH_2$—) included in the structure represented by $R^1$ to $R^{14}$ may be substituted with an oxygen atom (—O—), a carbonyl group (—CO—), an amino group (—NH— or —$NR^{28}$—), an ester group (—COO— or —OCO—), an amide group (—CONH— or —NHCO—), or a urethane group (—OCONH— or —NHCOO—).

$R^{15}$ to $R^{28}$ each independently represent an optionally substituted hydrocarbon group. Examples of the optionally substituted hydrocarbon group represented by $R^{15}$ to $R^{28}$ include a methyl group, an ethyl group, a propyl group, a butyl group, a phenyl group, a naphthyl group, and a benzyl group.

In this regard, $R^1$ to $R^{14}$ each independently preferably represent a hydrogen atom or an alkyl group having 1 to 8 carbon atoms, more preferably a hydrogen atom or an alkyl group having 1 to 4 carbon atoms, and particularly preferably a hydrogen atom or a methyl group.

$R^1$ to $R^8$ are particularly preferably hydrogen atoms, and $R^9$ to $R^{14}$ are particularly preferably methyl groups.

As the polyoxometalate anion represented by $B^{m-}$ a known polyoxometalate anion can be used.

Here, the polyoxometalate anion may be an isopolyoxometalate anion represented by $(M_pO_q)^{m-}$ or may be a heteropolyoxometalate anion represented by $(Z_pM_qO_r)^{m-}$ (in the formulae, Z represents a heteroatom, M represents a polyatom, O represents an oxygen atom, and p, q, and r represent the composition ratio of the respective atoms). Examples of the polyatom M include elements such as Mo, W, Ti, V, Nb, and Ta. Examples of the heteroatom Z include elements such as P, Si, B, As, Ge, S, Co, Zn, Al, and H.

Specifically, examples of the polyoxometalate anion include Keggin-type heteropolyoxometalate anions, such as $(PW_{12}O_{40})^{3-}$, $(SiW_{12}O_{40})^{4-}$, $(BW_{12}O_{40})^{5-}$, $(SW_{12}O_{40})^{2-}$, $(PMo_{12}O_{40})^{3-}$, $(SiMo_{12}O_{40})^{4-}$, $(BMo_{12}O_{40})^{5-}$, and $(SMo_{12}O_{40})^{2-}$; Dawson-type heteropolyoxometalate anions, such as $(P_2W_{18}O_{62})^{6-}$, $(Si_2W_{18}O_{62})^{8-}$, $(S_2W_{18}O_{62})^{4-}$, $(P_2Mo_{18}O_{62})^{6-}$, $(Si_2Mo_{18}O_{62})^{8-}$, and $(S_2Mo_{18}O_{62})^{4-}$; defect-type heteropolyoxometalate anions, such as $(PW_9O_{34})^{9-}$, $(PW_{10}O_{36})^{7-}$, $(PW_{11}O_{39})^{7-}$, $(PMo_9O_{34})^{9-}$, $(PMo_{10}O_{36})^{7-}$, $(PMo_{11}O_{39})^{7-}$, $(SiW_9O_{34})^{10-}$, $(SiW_{10}O_{36})^{8-}$, $(SiW_{11}O_{38})^{8-}$, $(SiMo_9O_{34})^{10-}$, $(SiMo_{10}O_{36})^{8-}$, $(SiMo_{11}O_{39})^{8-}$, $(P_2W_{17}O_{61})^{10-}$, $(P_2W_{15}O_{56})^{12-}$, $(H_2P_2W_{12}O_{48})^{12-}$, $(NaP_5W_{30}O_{110})^{14-}$, $(P_2Mo_{17}O_{61})^{10-}$, $(P_2Mo_{15}O_{56})^{12-}$, $(H_2Mo_2W_{12}O_{48})^{12-}$, and $(NaP_5Mo_{30}O_{110})^{-}$; isopolyoxometalate anions, such as $(WO_4)^{2-}$, $(W_6O_{19})^{2-}$, $(W_7O_{24})^{6-}$, $(W_{10}O_{32})^{4-}$, $(MoO_4)^{2-}$, $(Mo_6O_{19})^{2-}$, $(Mo_7O_{24})^{6-}$, and $(Mo_{10}O_{32})^{4-}$; and other various polyoxometalate anions, such as Strandberg-type, Anderson-type, Allman-Waugh-type, Weakley-Yamase-type, Dexter-Silverton-type, and Preyssler-type.

In the structure of the above-described polyoxometalate anion, those in which all or part of tungsten or molybdenum is substituted with at least one element selected from molybdenum, tungsten, titanium, vanadium, niobium, tantalum, iron, manganese, cobalt, nickel, and zinc, those in which all or part of phosphorus or silicon is substituted with at least one element selected from boron, arsenic, and germanium, and those in which all or part of tungsten or molybdenum is substituted with at least one selected from molybdenum, tungsten, titanium, vanadium, niobium, tantalum, iron, manganese, cobalt, nickel, and zinc and all or part of phosphorus or silicon is substituted with at least, one element selected from boron, arsenic, and germanium can also be similarly used.

The above-mentioned polyoxometalate anions can be used alone or in combination of two or more. In addition, isomers of the above-mentioned polyoxometalate anions distinguished as, for example, α-, β- , and γ- can be used alone or in combination of two or more.

Among the above, a polyoxometalate anion having a good hue in itself and suitable size and valence, capable of obtaining a stable solid state even when bonded to the dye structure of a cationic site, and hardly changing the hue as the compound is suitably used.

Such polyoxometalate anions represented by $B^{m-}$ are polyoxometalate anions at least including tungsten, and examples thereof include Keggin-type heteropolyoxometalate anions, such as $(PW_{12}O_{40})^{2-}$, $(SiW_{12}O_{40})^{4-}$, $(BW_{12}O_{40})^{5-}$, $(SW_{12}O_{40})^{2-}$, $(PMo_tW_{12-t}O_{40})^{3-}$, $(SiMo_tW_{12-t}O_{40})^{4-}$, $(BMo_tW_{12-t}O_{40})^{5-}$, and $(SMo_tW_{12-t}O_{40})^{2-}$; Dawson-type heteropolyoxometalate anions, such as $(P_2W_{18}O_{62})^{6-}$, $(Si_2W_{18}O_{62})^{8-}$, $(S_2W_{18}O_{62})^{4-}$, $(P_2Mo_tW_{18-t}O_{62})^{6-}$, $(Si_2Mo_tW_{18-t}O_{62})^{8-}$, and $(S_2Mo_tW_{18-t}O_{62})^{4-}$; defect-type heteropolyoxometalate anions, such as $(PW_9O_{34})^{9-}$, $(PW_{10}O_{36})^{7-}$, $(PW_{11}O_{39})^{7-}$, $(PMo_tW_{9-t}O_{34})^{9-}$, $(PMo_tW_{10-t}O_{36})^{7-}$, $(PMo_tW_{11-t}O_{39})^{7-}$, $(SiW_9O_{34})^{10-}$, $(SiW_{10}O_{36})^{8-}$, $(SiW_{11}O_{39})^{8-}$, $(SiMo_tW_{9-t}O_{34})^{10-}$, $(SiMo_tW_{10-t}O_{36})^{8-}$, $(SiMo_tW_{11-t}O_{39})^{8-}$, $(P_2W_{17}O_{61})^{10-}$, $(P_2W_{15}O_{56})^{12-}$, $(H_2P_2W_{12}O_{48})^{12-}$, $(NaP_5W_{30}O_{110})^{14-}$, $(P_2Mo_2W_{17}O_{61})^{10-}$, $(P_2Mo_tW_{15-t}O_{56})^{12-}$, $(H_2Mo_tW_{14-t}O_{48})^{12-}$, and $(NaP_5Mo_tW_{30-t}O_{110})^{14-}$; and isopolyoxometalate anions, such as $(WO_4)^{2-}$, $(W_6O_{19})^{2-}$, $(W_7O_{24})^{6-}$, and $(W_{10}O_{32})^{4-}$ (provided that t is 0 or a positive integer).

As a particularly suitable form, for example, a heteropolyoxometalate anion represented by $(PMo_yW_{12-y}O_{40})^{3-}$ in which y is an integer of 0, 1, 2, or 3 or a heteropolyoxometalate anion represented by $(SiMo_zW_{12-z}O_{40})^{4-}$ in which z is an integer of 0, 1, 2, or 3 is mentioned.

Specifically, the polyoxometalate anion represented by $B^{m-}$ is preferably $(PW_{12}O_{40})^{3-}$, $(PMoW_{11}O_{40})^{3-}$, $(SiW_{12}O_{40})^{4-}$, or $(SiMoW_{11}O_{40})^{4-}$, and examples of the compound including such a polyoxometalate anion include 12-tungsto(VI)phosphoric acid, 12-tungsto(VI)phosphoric acid n-hydrate, sodium 12-tungsto(VI)phosphate n-hydrate, potassium 12-tungsto(VI)phosphate n-hydrate, ammonium 12-tungsto(VI)phosphate n-hydrate, phosphotungstomolybdic acid, phosphotungstornolybdic acid n-hydrate, sodium phosphotungstomclybdate n-hydrate, potassium phosphotungstomclybdate n-hydrate, ammonium phosphotungstomolybdate n-hydrate, 12-tungsto(VI)silicic acid, 12-tungsto(VI)silicic acid n-hydrate, sodium 12-tungsto(VI)silicate n-hydrate, potassium 12-tungsto(VI)silicate n-hydrate, ammonium 12-tungsto(VI)silicate n-hydrate, silicotungstomolybdic acid, silicotungstomolybdic acid n-hydrate, sodium silicotungstomolybdate n-hydrate, potassium silicotungstomolybdate n-hydrate, and ammonium silicotungstomolybdate n-hydrate.

m represents an integer of 1 to 20, and n represents an integer of 1 to 20. When the optionally substituted alkyl group having 1 to 8 carbon atoms and the optionally substituted aromatic hydrocarbon group having 6 to 12 carbon atoms represented by $R^1$ to $R^{14}$ do not have a charge, m=n. In this case, m and n may be 3 or 4.

The optionally substituted alkyl group having 1 to 3 carbon atoms or the optionally substituted aromatic hydrocarbon group having 6 to 12 carbon atoms represented by $R^1$ to $R^{14}$ may have a charge. When the optionally substituted alkyl group having 1 to 8 carbon atoms or the optionally substituted aromatic hydrocarbon group having 6 to 12 carbon atoms represented by $R^1$ to $R^{14}$ has a charge, n is determined such that the charge of the whole formula (I) becomes zero.

The compound of the present invention is preferably a compound represented by the following formula (I-1):

[Chem. 3]

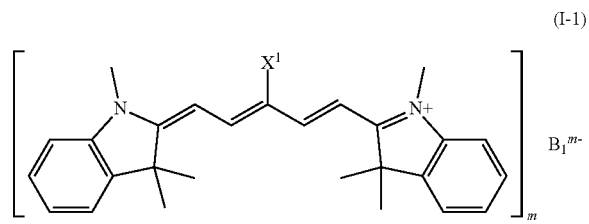

(I-1)

(in the formula (I-1), $X^1$ represents a methyl group, a chlorine atom, or a bromine atom;

$B_1^{m-}$ represents a heteropolyoxometalate anion represented by $(PMo_yW_{12-y}O_{40})^{3-}$ in which y is an integer of 0, 1, 2, or 3 or a heteropolyoxometalate anion represented by $(SiMo_zW_{12-z}O_{40})^{4-}$ in which z is an integer of 0, 1, 2, or 3; and m is 3 or 4).

$B_1^{m-}$ is preferably $(PW_{12}O_{40})^{3-}$, $(PMoW_{11}O_{40})^{3-}$, $(SiW_{12}O_{40})^{4-}$, or $(SiMoW_{11}O_{40})^{4-}$.

The compound or the present invention may be hydrate.

The compound of the present invention can be suitably used for forming a blue pixel portion of a color filter by having the above-mentioned structure.

Absorbance $A_{480}$ of colored film at wavelength of 480 nm (requirement 1)

From the viewpoint of obtaining an appropriate hue and a high luminance by transmitting light of a wavelength necessary as a blue pixel portion of a color filter, a lower absorbance $A_{480}$ of a colored film formed using the compound of the present invention at a wavelength of 480 nm is preferred. Specifically, when a colored film is formed using the compound of the present invention at a concentration of the compound of 26.6 mass % and a thickness of 1.0 μm, as the requirement 1, the absorbance $A_{480}$ of the colored film is preferably 0.25 or less and more preferably 0.20 or less.

Absorbance $A_{550}$ of colored film at wavelength of 550 nm (requirement 2)

From the viewpoint of obtaining an appropriate hue by shielding light of a wavelength unnecessary as a blue pixel portion of a color filter, a higher absorbance $A_{550}$ of a colored film formed using the compound of the present invention at a wavelength of 550 nm is preferred. Specifically, when a colored film is formed using the compound of the present invention at a concentration of the compound of 26.6 mass % and a thickness of 1.0 μm, as the requirement 2, the absorbance $A_{550}$ of the colored film is preferably 0.75 or more, more preferably 1.00 or more, further preferably 1.25 or more, and particularly preferably 1.50 or more.

Range in which Maximum Absorption Wavelength of Absorption Spectrum of Colored Film is Present (Requirement 3)

From the viewpoint of obtaining an appropriate hue by shielding light of a wavelength unnecessary as a blue pixel portion of a color filter, it is preferable that the absorption spectrum of a colored film formed using the compound of the present invention includes a maximum absorption in a wavelength range of 430 to 780 nm and that the maximum absorption wavelength $\lambda_x$ on the shortest wavelength side is within a wavelength range specified by the upper and lower limits shown below. Specifically, when a colored film is formed using the compound of the present, invention at a concentration of the compound of 26.6 mass % and a thickness of 1.0 μm, as a requirement 3-1, the lower limit of the range in which the maximum absorption wavelength of absorption spectrum of the colored film is present is preferably 500 nm, more preferably 520 nm, and particularly preferably 540 nm. In addition, as a requirement 3-2, the upper limit of the range in which the maximum absorption wavelength of absorption spectrum of the colored film is present is preferably 650 nm, more preferably 620 nm, and particularly preferably 600 nm.

Absorbance $A_x$ at Maximum Absorption Wavelength $\lambda_x$ on Shortest Wavelength Side (Requirement 4)

From the viewpoint of obtaining an appropriate hue and a high coloring power by shielding light of a wavelength unnecessary as a blue pixel portion of a color filter, in the absorption spectrum of a colored film formed using the compound of the present invention, a higher absorbance $A_x$ at the maximum absorption wavelength $\lambda_x$ on the shortest wavelength side in a wavelength range of 480 to 780 nm is preferred. Specifically, when a colored film is formed using the compound of the present invention at a concentration of the compound of 26.6 mass % and a thickness of 1.0 μm, as the requirement 4, the absorbance $A_x$ at the maximum absorption wavelength $\lambda_x$ on the shortest wavelength side in a wavelength range of 480 to 730 nm of the absorption spectrum of the colored film is preferably 1.10 or more, more preferably 1.50 or more, and particularly preferably 1.90 or more.

From the viewpoint of obtaining an appropriate hue and a high luminance, it is further preferable to satisfy both the requirement 1 and the requirement 2. From the viewpoint of obtaining an appropriate hue and high luminance and coloring power, it is further preferable to satisfy all the requirement 1, the requirements 3-1 and 3-2, and the requirement 4 or to satisfy all the requirement 2, the requirements 3-1 and 3-2, and the requirement 4. It is particularly to satisfy all the requirements 1 to 4.

In the above, although the characteristics of the spectrum of a colored film with a compound concentration of 26.6 mass % and a thickness of 1.0 μm have been described, the values of the above-mentioned requirements can also be applied to colored films of which either the concentration or the thickness is changed by converting the values according to the difference in the concentration or the thickness.

The compound of the present invention can easily prepare a colored film having a chromaticity (x, y) of (0.138, 0.090) in a C light source by having the above-mentioned structure, and the luminance of the colored film in a C light source at that time is high. Accordingly, the compound can be suitably used for forming a blue pixel portion of a color filter. In addition, since the compound of the present invention has a good hue and a high transmittance also for the design chromaticity of NCG (normal color gamut) or WCG (wide color gamut) other than the above, the compound can be suitably used for forming a blue pixel portion of a color filter. As the design chromaticity, (x, y), for example, (0.131, 0.046), (0.134, 0.100), (0.139, 0.090), (0.139, 0.080), (0.140, 0.060), (0.140, 0.080), (0.141, 0.091), (0.145, 0.080), (0.148, 0.060), (0.150, 0.060), (0.151, 0.073), (0.156, 0.065), (0.151, 0.073), and (0.156, 0.065) are mentioned.

It is inferred that in the compound of the present invention, a polyoxometalate anion binds to a dye having a hue suitable for forming a blue pixel portion of a color filter and can fix it in a suitable solid state, and the compound thereby expresses a high luminance even after a thermal history by post-bake. That is, since the dye molecule alone is not sufficiently stable for thermal history by post-bake, a suitable hue cannot be maintained, and as a result, it is difficult, to obtain a high luminance. On the other hand, in the compound of the present invention, a more stable crystalline state is realised by binding a dye molecule to a polyoxometalate anion, and a high luminance can be achieved without being decomposed or denatured even in thermal history of post-bake.

Here, whether a stable crystalline state is formed or not largely depends on the three-dimensional structure of a dye molecule. In particular, a polymethine chain, which is the central skeleton of a dye, becomes a large factor of controlling packing at the crystalline state, which depends on the presence or absence of a substituent. Accordingly, it is inferred that a polymethine chain having a substituent of an appropriate size at an appropriate position contributes to strengthening of the crystalline state when a dye is bound to a polyoxometalate anion. In this respect, it is conjectured that in the compound of the present, invention, the substituent X in the general formula (I) plays an important role of firmly fixing a polymethine chain in a crystalline state and thereby forming a more stable crystalline state to achieve a high luminance.

Incidentally, the three-dimensional structure of a polymethine chain as described above largely influences not only on the stability of the crystalline state but also on the hue as a solid. Accordingly, it is necessary to adjust the hue within a suitable range while improving the stability of the crystalline state, which are technically difficult problems. However, in the compound of the present invention, it is inferred that these problems are achieved by including a substituent with an appropriate size (of one atom excluding hydrogen atoms) at a limited position (the center of the polymethine chain) and thereby a high luminance is obtained.

The hue (absorption spectrum) of a dye itself and the hue (absorption spectrum) in a state of the dye bended to a polyoxometalate anion do not necessarily coincide with each other. This can be interpreted by the difference in the crystalline state as described above. That is, this is because that the conformation and the environment around the molecule as a dye itself and the conformation and the environment around the molecule in a state of the dye bonded to a polyoxometalate anion do not necessarily coincide with each other. Accordingly, it is necessary to pay attention also to the selection of the polyoxometalate anion so as to give an appropriate crystalline state after the bonding with a dye.

(Method for Synthesizing Compound Represented by General Formula (I))

The compound represented by the general formula (I) can be synthesized by chelating a dye represented by the following formula (II) with a polybasic acid or a polybacic acid salt including a polyoxometalate anion represented by $B^{m-}$. A water-soluble dye represented by the following formula (II) becomes the pigment of a water-insoluble compound represented by the general formula (I).

[Chem. 4]

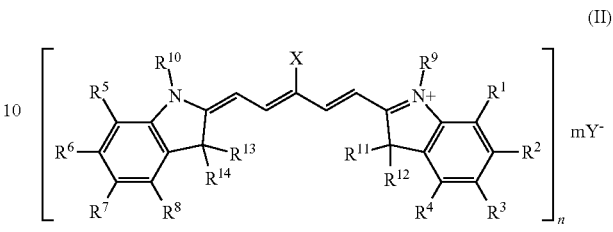

(II)

(In the formula (IT),

X represents a methyl group or a halogen atom;

$R^1$ to $R^{14}$ each independently represent a hydrogen atom, halogen atom, a cyano group, a nitro group, an optionally N-alkylated amino group or ammonium group, a hydroxy group, an allyloxy group, an alkoxy group, a sulfo group, an optionally N-alkylated sulfamoyl group, a carboxyl, group, an ester group, an optionally N-alkylated amide group, an optionally substituted hydrocarbon group having 1 to 12 carbon atoms, an optionally substituted aromatic hydrocarbon group having 6 to 12 carbon atoms, or an optionally substituted heterocyclic group having 3 to 12 carbon atoms, and adjacent two selected from $R^1$ to $R^4$, adjacent two selected from $R^5$ to $R^8$, $R^{11}$, and $R^{12}$, or $R^{13}$ and $R^{14}$ may be bonded to each other to form a ring;

$Y^-$ represents an anion;

m represents an integer of 1 to 20; and n represents an integer of 1 to 20, provided that n is determined such that the charge of the whole formula (I) becomes zero).

When the dye of which the anion $Y^-$ is a chloride ion is used and polybasic acid having a polyoxometalate anion represented by $B^{m-}$ is used, the compound represented by the general formula (I) can be manufactured by salt exchange through a dehydrochlorination reaction. When the dye of which the anion $Y^-$ is a chloride ion is used and a polybasic acid salt having a polyoxometalate anion represented by $B^{m-}$, for example, a polyoxometalate alkali metal salt, is used, the compound represented by the general formula (I) can be manufactured by salt exchange through a dealkali metal chloride reaction.

It is preferable to convert a polybasic acid once to a polyoxometalate alkali metal salt and then to perform a dealkali metal chloride reaction, because salt exchange can be certainly performed not only to give a compound with a higher yield but also to give a higher purity compound with, less by-products, compared to a dehydrochlorination reaction using the polybasic acid. Of course, the polyoxometalate alkali metal salt may be used after purification by, for example, recrystallization.

It is preferable to perform the above-mentioned reaction by charging heteropoly acid or a polyoxometalate alkali metal salt, which is used as an anion source of the compound of the present invention, in an amount such that the minus charge and the plus charge are equal numbers of moles according to the valence of the anion of the anion source and the valence of the cation of the dye. In addition, as needed, it is also possible to perform the reaction by adjusting the number of moles to be different from the equimolar number.

The dye represented by the formula (II) can also be synthesized by a known method, for example, a method described in "Functional Dye (kino-sei shikiso)" (Shin Ohkawara, et al., Kodansha Ltd., Published Mar. 10, 1992, pp. 98-117) or "Photopigment, (kanko shikiso)" (supervised by Masaaki Hayami, Sangyo Tosho Publishing Co., Ltd., Published Oct. 17, 1997, pp. 11-31). Alternatively, a commercially available dye can also be used.

For example, a dye of which $R^1$ to $R^8$ are hydrogen atoms, $R^9$ to $R^{14}$ are methyl groups, X is a methyl group, $Y^-$ is a paratoluene sulfonate anion, and m=n=1 and represented by the following formula is commercially available from Hayashibara Co., Ltd. under the name of NK-10374.

[Chem. 5]

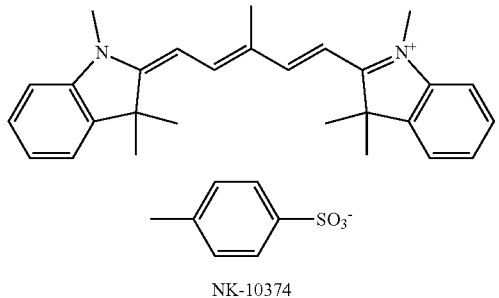

NK-10374

A dye of which $R^1$ to $R^8$ are hydrogen atoms, $R^9$ to $R^{14}$ are methyl groups, X is a chlorine atom, $Y^-$ is a paratoluene sulfonate anion, and m=n=1 and represented by the following formula is commercially available from Hayashibara Co., Ltd. under the name of NK-10739.

[Chem. 6]

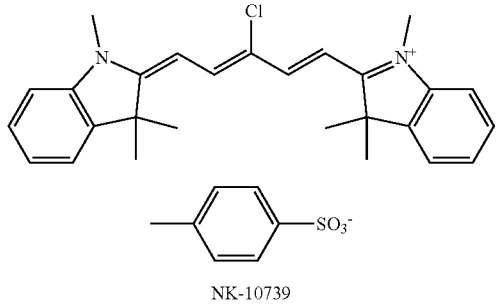

NK-10739

A dye of which $R^1$ to $R^8$ are hydrogen atoms, $R^9$ to $R^{14}$ are methyl groups, X is a bromine atom, $Y^-$ is a paratoluene sulfonate anion, and m=n=1 and represented by the following formula is commercially available from Hayashibara Co., Ltd. under the name of NK-10759.

[Chem. 7]

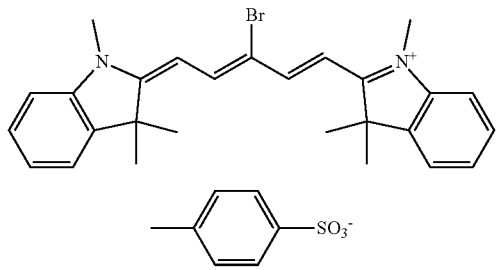

NK-10759

(Use of compound represented by general formula (I))

The compound of the present invention can be used in a blue pixel portion of a color filter by being prepared into a photosensitive composition for a color filter by a known method.

When the compound of the present invention is used in a blue pixel portion of a color filter, pigment dispersion in a photosensitive composition for the color filter is easy, the light shielding property at 365 nm, which is frequently used when the photosensitive composition for a color filter is cured, is decreased, the photocuring sensitivity of a resist is not decreased, and film reduction and pattern flowing at the time of developing are unlikely to occur. A blue pixel portion of a color filter with high sharpness and luminance that have been demanded in recent years can be more easily obtained.

The color filter of the present invention can be obtained by at least adding the compound of the present invention to a blue pixel portion of the color filter. In the color filter field, the handling of saturation values is very strict, unlike usual general use such as printing ink or paint, and it is difficult to improve the saturation values, even if it is very slight. However, the color purity is improved by using the compound of the present invention in preparation of a color filter to give a liquid crystal display with a wider RGB color reproduction range.

Since a pigment composition containing the compound of the present invention has a higher coloring power, if the color density is the same, advantageously, a smaller amount can be used, and the transmittance can also be increased.

The compound of the present invention can be used alone as it is in manufacturing a blue pixel portion of a color filter, but may be used in combination, as needed, considering economic efficiency, with a blue pigment, such as C.I. Pigment Blue 15, 15:3, 15:4, 15:6, or 60; a violet pigment, such as C.I. Pigment Violet 1, 13, 23, 29, 32, 36, or 38; a red dye, such as C.I. Acid Red 1, 4, 8, 14, 17, 18, 26, 27, 29, 31, 34, 35, 37, 42, 44, 50, 51, 52, 57, 66, 73, 87, 88, 51, 92, 94, 97, 103, 111, 114, 129, 133, 134, 138, 143, 145, 150, 151, 158, 176, 182, 133, 195, 198, 206, 211, 215, 216, 217, 227, 228, 249, 252, 257, 258, 260, 261, 266, 263, 270, 274, 277, 230, 281, 289, 308, 312, 315, 316, 339, 341, 345, 346, 349, 332, 383, 388, 394, 401, 412, 417, 413, 422, or 426, C.I. Direct Red 79, 82, 83, 84, 91, 92, 96, 97, 98, 99, 105, 106, 107, 172, 173, 176, 177, 179, 131, 132, 184, 204, 207, 211, 213, 218, 220, 221, 222, 232, 233, 234, 241, 243, 246, or 250, C.I. Basic Red 1 or 10, C.I. Reactive Red 36, or C.I. Mordant Red 1, 2, 4, 9, 12, 14, 17, 18, 19, 22, 23, 24, 25, 26, 27, 30, 32, 33, 36, 37, 38, 39, 41, 43, 45, 46, 48, 53, 56, 63, 71, 74, 85, 86, 88, 90, 94, or 95; a violet dye, such as C.I. Acid Violet 6B, 1, 9, 17, 19, 30, or 102, C.I. Direct Violet 47, 52, 54, 59, 60, 65, 66, 79, 30, 81, 82, 84, 89, 90, 93, 95, 96, 103, or 104, or C.I. Mordant Violet 1, 2, 4, 5, 7, 14, 22, 24, 30, 31, 32, 37, 40, 41, 44, 45, 47, 48, 53, or 58; a blue dye, such as C.I. Acid Blue 1, 7, 9, 15, 18, 22, 29, 42, 59, 60, 62, 70, 72, 74, 32, 83, 86, 87, 90, 92, 93, 100, 102, 103, 104, 113, 117, 120, 126, 130, 131, 142, 147, 151, 154, 153, 161, 166, 167, 168, 170, 171, 184, 187, 192, 199, 210, 229, 234, 236, 242, 243, 256, 259, 267, 285, 296, 315, or 335, C.I. Direct Blue 1, 2, 6, 8, 15, 22, 25, 41, 57, 71, 76, 78, 80, 81, 84, 85, 86, 90, 93, 94, 95, 97, 98, 99, 100, 101, 106, 107, 108, 109, 113, 114, 115, 117, 119, 120, 137, 149, 150, 153, 155, 156, 158, 159, 160, 161, 162, 163, 164, 165, 166, 167, 168, 170, 171, 172, 173, 188, 189, 190, 192, 193, 194, 195, 196, 193, 199, 200, 201, 202, 203, 207, 209, 210, 212, 213, 214, 222, 225, 226, 223, 229, 236, 237, 238, 242, 243, 244, 245, 246, 247, 248, 249, 251, 252, 256, 257, 259, 260, 268, 274, 275, or 293, C.I. Basic Blue 1, 3, 5, 7, 9, 19, 24, 25 26, 28, 29, 40, 41, 54, 58, 59, 64, 65, 66, 67, or 68, C.I. Mordant Blue 1, 2, 3, 7, 9, 12, 13, 15, 16, 19, 20, 21, 22, 26, 30, 31, 39, 40, 41, 43, 44, 49, 53, 61, 74, 77, 33, or 84, or C.I. Vat Blue 1, 4, 5, 6, 17, 18, 20, 35, or 66; or another well-known and commonly used blue, violet, or red pigment or dye or a derivative thereof. A well-known and commonly used pigment or dye with another color or a derivative thereof may be used in combination with the compound within a range that does not impair, for example, luminance, contrast, or reliability.

The compound of the present invention can be used for forming a pattern of a blue pixel portion of a color filter by a known method. For example, although it is possible to prepare an ink jet recording ink for forming a blue pixel portion of a color filter containing the compound of the present invention, a dispersant, a thermosetting resin binder, and an organic solvent, typically, a photosensitive composition for a blue pixel portion of a color filter can be obtained by containing the compound of the present invention and a photosensitive resin as essential components.

For example, a photosensitive composition for a blue pixel portion of a color filter can be prepared by mixing the compound of the present invention, a photosensitive resin, a photopolymerization initiator, and an organic solvent dissolving the resin as essential components. Alternatively, a photosensitive composition for a blue pixel portion of a color filter can be prepared by preparing a dispersion using the compound of the present invention, an organic solvent, and, as needed, a dispersant and then adding a photosensitive resin, etc. to the dispersion.

Examples of the dispersant that is used as needed include products of BYK-Chemie: Disperbyk (registered trademark) 101, 103, 107, 108, 110, 111, 116, 130, 140, 154, 161, 162, 163, 164, 165, 166, 170, 171, 174, 180, 181, 182, 183, 184, 185, 190, 2000, 2001, 2020, 2025, 2050, 2070, 2095, 2150, 2155, and 2164, and BYK (registered trademark)-LPN6919 and 21116; products of Lubrizol Japan Limited: SOL-SPERSE (registered trademark)-3000, 9000, 13000, 13240, 13650, 13940, 16000, 17000, 18000, 20000, 21000, 24000, 26000, 27000, 28000, 31845, 32000, 32500, 32550, 33500, 32600, 34750, 35100, 36600, 38500, 41000, 41090, 53095, 55000, and 76500; products of BASF Japan Ltd.: Efka (registered trademark) 46, 47, 48, 452, 4008, 4009, 4010, 4015, 4020, 4047, 4050, 4055, 4060, 4080, 4400, 4401, 4402, 4403, 4406, 4408, 4300, 4310, 4320, 4330, 4340, 450, 451, 453, 4540, 4550, 4560, 4800, 5010, 5065, 5066, 5070, 7500, 7554, 1101, 320, 150, 1501, 1502, and 1503; and products manufactured by Ajinomoto Fine-Techno Co., Ltd.: AJISPER (registered trademark) PA111, PB711, PB821, PB822, and PB824. In addition, a leveling agent, a coupling agent, a cationic surfactant, or the like can also be used in combination.

When a dispersion is prepared using the compound of the present, invention, a pigment, derivative can also be used as a dispersing auxiliary agent as needed.

When the compound of the present invention and C.I. Pigment Blue 15:6 are co-dispersed, among the dispersants that are used as needed, a dispersant with, high base number and polarity, such as Disperbyk 2000, can be particularly suitably used.

Examples of the organic solvent include aromatic solvents, such as toluene, xylene, and methoxybenzene; acetic acid ester solvents, such as ethyl acetate, butyl acetate, propylene glycol monomethyl ether acetate, propylene glycol monoethyl ether acetate, dipropylene glycol methyl ether acetate, and 3-methoxybutyl acetate; propionate solvents, such as ethoxyethyl propionate; lactic acid ester solvents, such as ethyl lactate; alcoholic solvents, such as methanol and ethanol; ether solvents, such as butyl cellosolve, propylene glycol monomethyl ether, diethylene glycol ethyl ether, diethylene glycol dimethyl ether, ethylene glycol monobutyl ether, and 3-methoxy-1-butanol; ketone solvents, such as methyl ethyl ketone, methyl isobutyl ketone, and cyclohexanone; aliphatic hydrocarbon solvents, such as hexane; nitrogen compound based solvents, such as N,N-dimethylformamide, γ-butyrolactam, N-methyl-2-pyrrolidone, aniline, and pyridine; lactone solvents, such as γ-butyrolactone; solvents having a plurality of functional groups, such as a carbamic acid ester, e.g., a mixture of methyl carbamate and ethyl carbamate at 48:52, and diacetone alcohol; and water-containing solvents, such as water. As the organic solvent, particularly suitable are propylene glycol monomethyl ether acetate, propylene glycol monomethyl ether, ethylene glycol monobutyl ether, dipropylene glycol methyl ether acetate, ethyl lactate, 3-methoxybutyl acetate, 3-methoxy-1-butanol, ethoxyethyl propionate, cyclohexanone, and N-methyl-2-pyrrolidone.

The above-mentioned dispersion can be obtained by stirring and dispersing 100 to 5000 parts by mass of an organic solvent and as needed, 0 to 200 parts by mass of a dispersant and/or 0 to 50 parts by mass of a pigment derivative based on 100 parts by mass of the compound of the present invention to a uniform dispersion. A photosensitive composition for a blue pixel portion of a color filter can be obtained by subsequently adding to this dispersion 10 to 500 parts by mass of a photosensitive resin based on 100 parts by mass of the compound of the present invention, 5 to 100 parts by mass of a photopolymerization initiator based on 100 parts by mass of the photosensitive resin, and as needed, an organic solvent and stirring and dispersing the mixture until uniform. Such a photosensitive composition may be called a color resist.

Examples of the photosensitive resin that can be used on this occasion include thermoplastic resins, such as a urethane resin, an acrylic resin, a polyamic acid resin, a polyimide resin, a styrene-maleic acid resin, and a styrene-maleic anhydride resin; and photopolymerizable monomers, for example, bifunction monomers, such as 1,6-hexanediol diacrylate, ethylene glycol diacrylate, neopentyl glycol diacrylate, triethylene glycol diacrylate, bis(acryloxyethoxy)bisphenol A, and 3-methylpentanediol diacrylate, and multifunctional monomers, such as trimethylolpropatone triacrylate, pentaerythritol triacrylate, pentaerythritol tetraacrylate, tris(2-hydroxyethyl)isocyanurate triacrylate, dipentaerythritol hexaacrylate, and dipentaerythritol pentaacrylate.

Examples of the photopolymerization initiator include acetophenone-based compounds, such as 4-phenoxydichloroacetophenorle, 4-tert-butyl-dichloroacetophenone, diethoxyacetophenone, 1-(4-isopropylphenyl)-2-hydroxy-2-methylpropan-1-one, 1-hydroxycyclohexyl phenyl ketone, 2-methyl-1-[4-(methylthio)phenyl]-2-morpholinopropan-1-one, 2-(dimethylamino)-2-[(4-methylphenyl)methyl]-1-[4-(4-morpholinyl)phenyl]-1-butanone, and 2-benzyl-2-dimethylamino-1-(4-morpholinophenyl)-bunan-1-one; benzoin-based compounds, such as benzoin, benzoin methyl ether, benzoin ethyl ether, benzoin isopropyl ether, and benzyl dimethyl ketal; benzophenone-based compounds, such as benzophenone, benzoylbenzoic acid, methyl benzoylbenzoate, 4-phenylbenzophenone, hydroxybenzophenone, acrylated benzophenone, 4-benzoyl-4'-methyldiphenyl sulfide, and 3,3',4,4'-tetra(tert-butylperoxycarbonyl)benzophenone; thioxarithone-based compounds, such as thioxanthone, 2-chlorothioxanthone, 2-methylthioxanthone, isopropylthioxanthone, 2,4-diisopropylthioxanthone, and 2,4-diethyithioxanthone; triazine-based compounds, such as 2,4,6-trichloro-1,3,5-triazirie, 2-phenyl-4,6-bis(trichloromethyl)-1,3,5-triazine, 2-(p-methoxyphenyl)-4,6-bis(trichloromethyl)-1,3,5-triazine, 2-(p-tolyl)-4,6-bis(trichloromethyl)-1,3,5-triasine, 2-piperonyl-4,6-bis(trichloromethyl)-1,3,5-triazine, 2,4-bis(trichloromethyl)-6-styryl-1,3,5-triazine, 2-(naphtho-1-yl)-4,6-bis(trichloromethyl)-1,3,5-triazine, 2-(4-methoxy-naphtho-1-yl)-4,6-bis(trichloromethyl)-1,3,5-triazine, 2,4-trichloromethyl-(piperonyl)-6-triazine, and 2,4-trichioromethyl-(4'-methoxystyryl)-6-triazine; oxime ester-based compounds, such as 1-(N-4-benzoylphenyl-carbazol-3-yl)-butane-1,2-dione-2-oxixne-O-acetate, 1,2-octanedione, 1-[4-(phenylthio)2-(O-benzoyloxime)], ethanone, 1-[9-ethyl-6-(2-methylbenzoyl)-9H-carbazol-3-yl],1-(O- acetyloxime), and O-(acetyl)-N-(1-phenyl-2-oxo-2-(4'-methoxy-naphthyl)ethylidene)hydroxylamine; phosphine-based compounds, such as bis(2,4,6-trimethylbenzoyl) phenyiphosphine oxide and 2,4,6-trimethylbenzoyl diphenylphosphine oxide; quinone-based compounds, such as 9,10-phenanthrene quinone, camphor quinone, and ethyl anthraquinone; borate-based compounds; carbazole-based compounds; imidazole-based compounds; and titanocene-based compounds.

As needed, for example, a surfactant, a polymerization inhibitor, an antioxidant, a sensitizer, and a light-resistant stabilizer may be further added to the above-mentioned photosensitive composition.

The thus-prepared photosensitive composition for a blue pixel portion of a color filter is subjected pattern exposure with ultraviolet light through a photomask, and the unexposed portion is then washed with an organic solvent or an alkaline water to make a color filter.

Examples of the method for manufacturing a color filter include a method called photolithography in which the compound of the present invention and a photosensitive composition for a blue pixel portion are applied onto a transparent substrate, such as glass, by a spin coating method, a slit coating method, a roll coating method, an ink jet method, or the like, this coated layer is then subjected to pattern exposure with ultraviolet light through a photomask, and the unexposed portion is then washed with a solvent or the like to obtain a blue pattern.

The color filter may be manufactured by forming a pattern of a blue pixel portion by another method, e.g., an electrodeposition method, a decalcomania method, a micelle electrolysis method, or a PVED (Photovoltaic Electrodeposition) method. Incidentally, a pattern of a red pixel portion and a pattern of a green pixel portion can also be formed by the same method using known pigments. The compound of the present invention has little decrease in luminance when it receives a thermal history or a light, history and is therefore significantly useful in a method for manufacturing a color filter including, for example, a baking step.

The compound of the present invention can be used in formation of a pixel portion of a color filter by a known method. A typical method as the method for dispersing the compound of the present invention is a photolithography method, which is a method in which a photosensitive composition described later is applied on the surface of a transparent substrate for a color filter on the side provided with a black matrix and is heat dried (prebake) and is then subjected to pattern exposure by irradiation with ultraviolet light through a photomask to cure the photosensitive composition at the portion corresponding to the pixel portion, the unexposed portion is then developed with a developing solution, arid the non-pixel portion is removed to fix the pixel portion to the transparent substrate. In this method, a pixel portion made of a cured colored film of a photosensitive composition is formed on a transparent substrate.

Regarding red and green colors, the above-described photosensitive compositions are prepared, and the above-described procedure is repeated. Thus, a color filter including red, green, and blue colored pixel portions at predetermined positions can be manufactured. Incidentally, in order to prepare photosensitive compositions for forming the red pixel portion and the green pixel portion, well-known and commonly used red pigment and green pigment can be used.

The compound of the present invention has a higher coloring power and produces a bright blue color with a high color purity. Accordingly, the compound is also suitable for coloring, such as paint, plastic, printing ink, rubber, leather, printing, electronic toner, jet ink, and thermal transfer ink, in addition to that for a color filter described in detail above.

EXAMPLES

The present invention will now be described in detail by Examples but is not limited by the following description.
(Preparation of Polyoxometalate Salt)

Preparation Example 1

Phosphotungatomolybdic acid (PWM-11-1, manufactured by Nippon Inorganic Colour & Chemical Co., Ltd., 30 g) was dissolved in purified water (75 mL), and sodium chloride (manufactured by Kanto Chemical Co., Inc., 15 g) was added to the solution while stirring at room temperature. After stirring for 1 hour, the resulting precipitate was filtered and washed with 2 mol/L sodium chloride aqueous solution. The residue was dried under reduced pressure to obtain sodium phosphotungstomolybdate hydrate ([$Na_3$ ($PMoW_{11}O_{40}$)·$xH_2O$], 16.34 g).
(Preparation of Polyoxometalate Salt)

Preparation Example 2

One mol/L $Na_2MoO_4$ aqueous solution (16.4 mL) was added to 13 mol/L $HNO_3$ aqueous solution (9.8 mL), followed by stirring. To this solution, 16.4 g of $K_8$ ($SiW_{11}O_{39}$) ·$13H_2O$ prepared by the method described in Literature 1 mentioned below was added little by little. After stirring at room temperature for 4 hours, a saturated KCl aqueous solution (26 mL) was added thereto to obtain precipitate. This precipitate was collected by filtration and was washed with a saturated KCl aqueous solution. The resulting solid was dried at room temperature under reduced pressure to obtain potassium silicotungstomolybdate hydrate ([K$_4$(SiMoW$_{11}$O$_{40}$)·xH$_2$O], 12.2 g).
(Literature 1: INORGANIC SYNTHESES, vol. 27, p. 85)

(Synthesis of Color Material Compound of Example 1)

Synthesis Example 1

A glass flask equipped with a stirrer, a thermometer, a cooling tube, and a dropping device was charged with the following compound NK-10374 (manufactured by Havashibara Co., Ltd., 2.00 g) and a solvent mixture (269 g) of water and methanol (1:1), followed by stirring at 50° C. for 30 minutes for dissolution.

[Chem. 8]

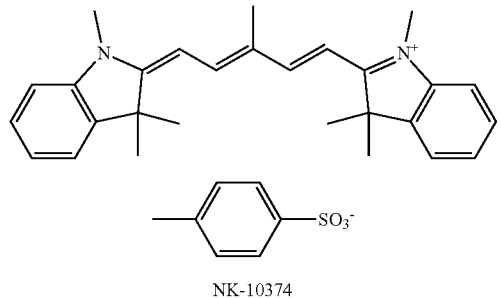

NK-10374

Subsequently, a solution prepared by dissolving sodium 12-tungsto(VI) phosphate n-bydrate (manufactured by FUJIFILM Wako Pure Chemical Corporation, 4.31 g) in a solvent mixture (31 g) of water and methanol (1:1) was dropwise added over 30 minutes with the dropping device. After completion of the dropwise addition, stirring was further performed at 50° C. for 90 minutes for insolubilization. After cooling t room temperature, filtration was performed, arid the solid collected by filtration was peptized with pure water (400 mL), followed by stirring for 30 minutes. Filtration was performed again, followed by washing with 200 mL of pure water. The resulting solid was dried at 90° C. for 16 hours obtain compound 1 (4.72 g) represented by the following formula (1).

[Chem. 9]

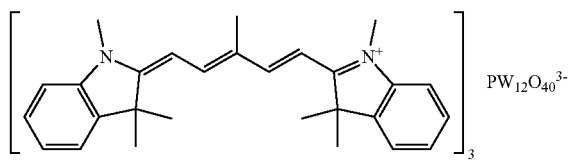

(1)

(Synthesis of Color Material Compound of Example 2)

Synthesis Example 2

A glass flask equipped with a stirrer, a thermometer, a cooling tube, and a dropping device was charged with the above-mentioned compound NK-10374 (manufactured by Hayashibara Co., Ltd., 2.00 g) and a solvent mixture (269 g) of water and methanol (1:1), followed by stirring at 50° C. for 30 minutes for dissolution. Subsequently, a solution prepared by dissolving sodium phosphotungstomolybdate hydrate (3.97 g) of Preparation Example 1 in a solvent mixture (31 g) of water and methanol (1:1) was dropwise added over 30 minutes with the dropping device. After completion of the dropwise addition, stirring was further performed at 50° C. for 90 minutes for insolubilization. After cooling to room temperature, filtration was performed, and the solid collected by filtration was peptized with pure water (400 mL), followed by stirring for 30 minutes. Filtration was performed again, followed by washing with 200 mL of pure water. The resulting solid was dried at 90° C. for 16 hours to obtain compound 2 (4.72 g) represented by the following formula (2).

[Chem. 10]

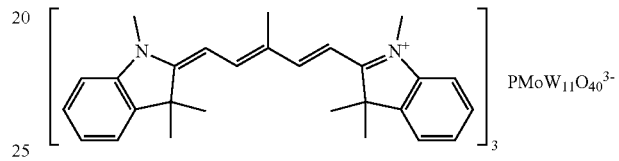

(2)

(Synthesis of Color Material Compound of Example 3)

Synthesis Example 3

A glass flask equipped with a stirrer, a thermometer, a cooling tube, and a dropping device was charged with the above-mentioned compound NK-10374 (manufactured by Hayashibara Co., Ltd., 2.50 g) and a solvent mixture (336 g) of water and methanol (1:1), followed by stirring at 50° C. for 30 minutes for dissolution. Subsequently, a solution prepared by dissolving potassium silicotungstomolybdate hydrate (3.49 g) of Preparation Example 2 in a solvent mixture (25 g) of water and methanol (1:1) was dropwise added over 30 minutes with the dropping device. After completion of the dropwise addition, stirring was further performed at 50° C. for 90 minutes for insolubilization. After cooling to room temperature, filtration was performed, and the solid collected by filtration was peptized with pure water (200 mL), followed by stirring for 30 minutes. Filtration was performed again, followed by washing with 200 mL of pure water. The resulting solid was dried at 90° C. for 16 hours to obtain compound 3 (4.65 g) represented by the following formula (3).

[Chem. 11]

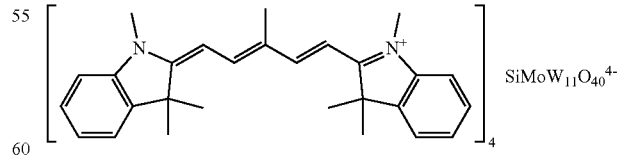

(3)

(Synthesis of Color Material Compound of Example 4)

Synthesis Example 4

A glass flask, equipped with a stirrer, a thermometer, a cooling tube, and a dropping device was charged with the following compound NK-1073S (manufactured by Hayashibara Co., Ltd., 2.50 g) and a solvent mixture (375 g) of water and methanol (1:1), followed by stirring at 50° C. for 30 minutes for dissolution.

[Chem. 12]

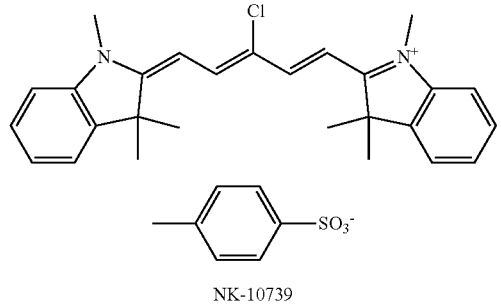

NK-10739

Subsequently, a solution prepared by dissolving sodium 12-tungsto(VI)phosphate n-hydrate (manufactured by FUJIFILM Wako Pure Chemical Corporation, 5.19 g) in a solvent, mixture (42 g) of water and methanol (1:1) was dropwise added over 30 minutes with the dropping device. After completion of the dropwise addition, stirring was further performed at 50° C. for 90 minutes for insolubilization. After coaling to room temperature, filtration was performed, followed by washing with 300 mL of pure water three times. The solid collected by filtration was peptized with pure water (200 mL), followed by stirring for 30 minutes and then filtration again. The resulting solid was dried at 90° C. for 16 hours to obtain compound 4 (5.64 g) represented by the following formula (4).

[Chem. 13]

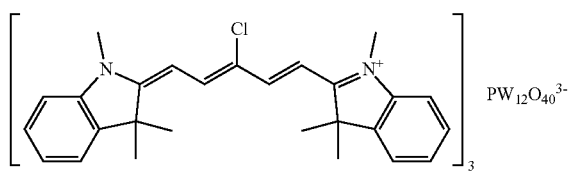

(4)

(Synthesis of Color Material Compound of Example 5)

Synthesis Example 5

A glass flask equipped with a stirrer, a thermometer, a cooling tube, and a dropping device was charged with the above-mentioned compound NK-10739 (manufactured by Hayashibara Co., Ltd., 2.00 g) and a solvent mixture (300 g) of water and methanol (1:1), followed by stirring at 50° C. for 30 minutes for dissolution. Subsequently, a solution prepared by dissolving phosphotungstomolybdic acid (PWM-11-1, manufactured by Nippon Inorganic Colour & Chemical Co., Ltd., 3.83 g) in a solvent mixture (31 g) of water and methanol (1:1) was dropwise added over 30 minutes with the dropping device. After completion of the dropwise addition, stirring was further performed at 50° C. for 90 minutes for insolubilization. After cooling to room temperature, filtration was performed, followed by washing with 150 mL of pure water three times. The solid collected by filtration was peptized with pure water (200 mL), followed by stirring for 30 minutes. Filtration was performed again, and the resulting solid was dried at 90° C. for 16 hours to obtain compound 5 (4.42 g) represented by the following formula (5).

[Chem. 14]

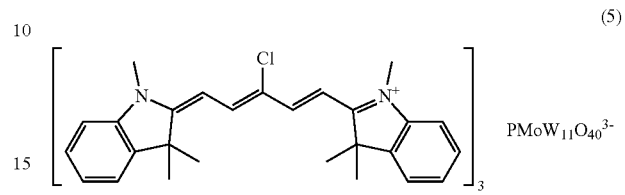

(5)

(Synthesis of Color Material Compound of Example 6)

Synthesis Example 6

A glass flask equipped with a stirrer, a thermometer, a cooling tube, and a dropping device was charged with the above-mentioned compound NK-10739 (manufactured by Hayashibara Co., Ltd., 2.00 g) and a solvent mixture (300 g) of water and methanol (1:1), followed by stirring at 50° C. for 30 minutes for dissolution. Subsequently, a solution prepared by dissolving sodium silicotungstate dodecahydrate (manufactured by Mitsuwa Chemical Co., Ltd., 2.84 g) in a solvent mixture (36 g) of water and methanol (1:1) was dropwise added over 30 minutes with the dropping device. After completion of the dropwise addition, stirring was further performed at 50° C. for 90 minutes for insolubilization. After cooling to room temperature, filtration was performed, followed by washing with 150 mL of pure water three times. The solid collected by filtration was peptized with pure water (200 mL), followed by stirring for 30 minutes. Filtration was performed again, and the resulting solid was dried at 90° C. for 16 hours to obtain compound 6 (3.39 g) represented by the following formula (6).

[Chem. 15]

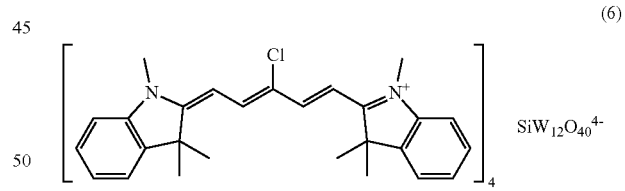

(6)

(Synthesis of Color Material Compound of Example 7)

Synthesis Example 7

A glass flask equipped with a stirrer, a thermometer, a cooling tube, and a dropping device was charged with the above-mentioned compound NK-10739 (manufactured by Hayashibara Co., Ltd., 2.00 g) and a solvent mixture (375 g) of water and methanol (1:1), followed by stirring at 50° C. for 30 minutes for dissolution. Subsequently, a solution prepared by dissolving potassium silicotungstomolybdate hydrate (3.37 g) of Preparation Example 2 in a solvent mixture (27 g) of water and methanol (1:1) was dropwise added over 30 minutes with the dropping device. After completion of the dropwise addition, stirring was further performed at 50° C. for 90 minutes for insolubilization. After cooling to room temperature, filtration was performed, followed by washing with 150 mL of pure water three times. The solid collected by filtration was peptized with pure water (200 mL), followed by stirring for 30 minutes. Filtration was performed again, and the resulting solid was dried at 90° C. for 16 hours to obtain compound 7 (4.29 g) represented by the following formula (7).

[Chem. 16]

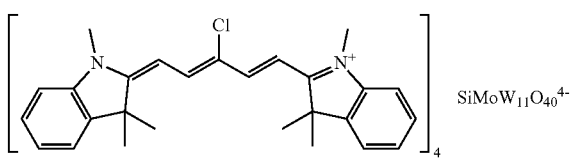
(7)

(Synthesis of Color Material Compound of Example 8)

Synthesis Example 8

A glass flask equipped with a stirrer, a thermometer, a cooling tube, and a dropping device was charged with the following compound NK-10759 (manufactured by Hayashibara Co., Ltd., 2.50 g) and a solvent mixture (375 g) of water and methanol (1:1), followed by stirring at 50° C. for 30 minutes for dissolution.

[Chem. 17]

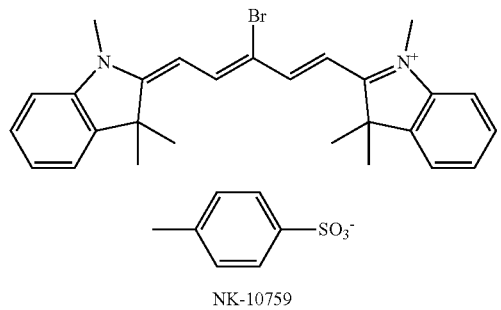

NK-10759

Subsequently, a solution prepared by dissolving sodium 12-tungsto(VI)phosphate n-hydrate (manufactured by FUJIFILM Wako Pure Chemical. Corporation, 4.83 g) in a solvent mixture (60 g) of water and methanol (1:1) was dropwise added over 30 minutes with the dropping device. After completion of the dropwise addition, stirring was further performed at 50° C. for 90 minutes for insolubilization. After cooling to room temperature, filtration was performed, followed by washing with 150 mL of pure water. The solid collected by filtration was peptized with pure water (200 mL), followed by stirring for 30 minutes. After stirring, filtration was performed again, followed by washing with 150 mL of pure water. The resulting solid was dried at 90° C. for 16 hours to obtain compound 8 (5.59 g) represented by the following formula (8).

[Chem. 18]

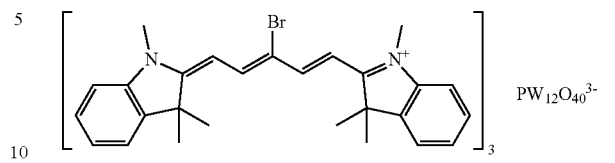
(8)

(Synthesis of Color Material Compound of Comparative Example 4)

Synthesis Example 9

A glass flask equipped with a stirrer, a thermometer, a cooling tube, and a dropping device was charged with the following compound NK-10043 (manufactured by Hayashibara Co., Ltd., 1.50 g) and a solvent mixture (225 g) of water and methanol (1:1), followed by stirring at 50° C. for 30 minutes for dissolution.

[Chem. 19]

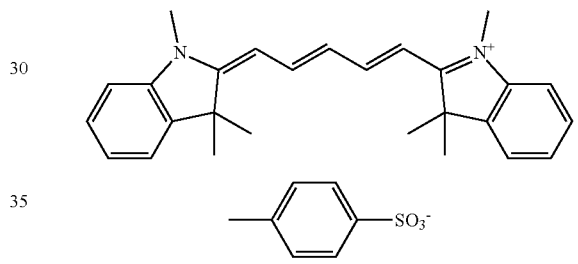

NK-10043

Subsequently, a solution prepared by dissolving sodium 12-tungsto(VI)phosphate n-hydrate (manufactured by FUJIFILM Wako Pure Chemical Corporation, 3.31 g) in a solvent mixture (26 g) of water and methanol (1:1) was dropwise added over 30 minutes with the dropping device. After completion of the dropwise addition, stirring was further performed at 50° C. for 90 minutes for insolubilization. After cooling to room temperature, filtration was performed. The solid collected by filtration was peptized with pure water (200 mL), followed by stirring for 60 minutes. After stirring, filtration was performed again, followed by washing with 200 mL of pure water. The resulting solid was dried at 90° C. for 16 hours to obtain compound 9 (2.96 g) represented by the following formula (9).

[Chem. 20]

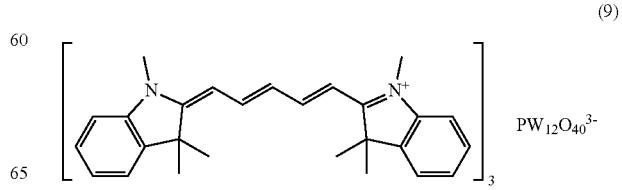
(9)

(Synthesis of Color Material Compound of Comparative Example 5)

Synthesis Example 10

A glass flask equipped with a stirrer, a thermometer, a cooling tube, and a dropping device was charged with the following compound NK-9419 (manufactured by Hayashibara Co., Ltd., 1.50 g) and a solvent mixture (225 g) of water and methanol (1:1), followed by stirring at 50° C. for 30 minutes for dissolution.

[Chem. 21]

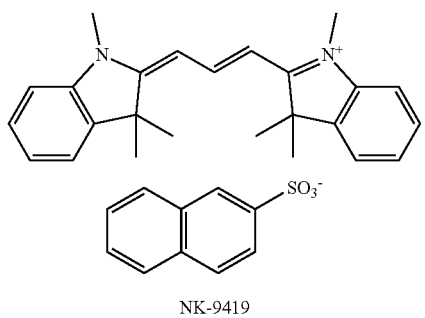

NK-9419

Subsequently, a solution prepared by dissolving sodium 12-tungsto(VI)phosphate n-hydrate (manufactured by FUJIFILM Wako Pure Chemical Corporation, 3.25 g) in a solvent mixture (26 g) of water and methanol (1:1) was dropwise added over 30 minutes with the dropping device. After completion of the dropwise addition, stirring was further performed at 50° C. for 90 minutes for insolubilization. After cooling to room temperature, filtration was performed. The solid collected by filtration was peptized with pure water (200 mL), followed by stirring for 60 minutes. After stirring, filtration was performed again, followed by washing with 200 mL of pure water. The resulting solid was dried at 90° C. for 16 hours to obtain compound 10 (3.01 g) represented by the following formula (10).

[Chem. 22]

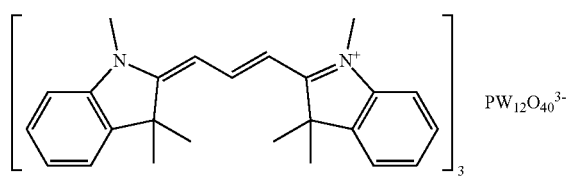

(10)

(Synthesis of Color Material Compound of Comparative Example 5)

Synthesis Example 11

A glass flask equipped with a stirrer, a thermometer, a cooling tube, and a dropping device was charged with the following compound NK-5559 (manufactured by Hayashibara Co. Ltd., 2.00 g) and a solvent mixture (300 g) of water and methanol (1:1), followed by stirring at 50° C. for 30 minutes for dissolution.

[Chem. 23]

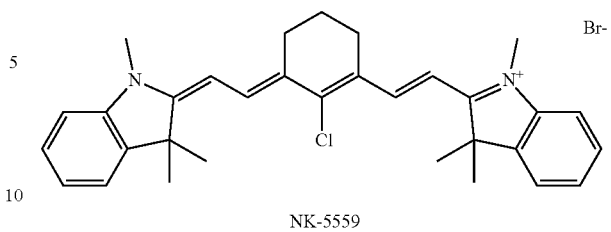

NK-5559

Subsequently, a solution prepared by dissolving sodium 12-tungsto(VI)phosphate n-hydrate (manufactured by FUJIFILM Wako Pure Chemical Corporation, 4.34 g) in a solvent mixture (35 g) of water and methanol (1:1) was dropwise added over 30 minutes with the dropping device. After completion of the dropwise addition, stirring was further performed at 50° C. for 90 minutes for insolubilization. After cooling to room temperature, filtration was performed. The solid collected by filtration was peptized with pure water (200 mL), followed by stirring for 60 minutes. After stirring, filtration was performed again, followed by washing with 200 mL of pure water. The resulting solid was dried at 90° C. for 16 hours to obtain compound 11 (4.92 g) represented by the following formula (11).

[Chem. 24]

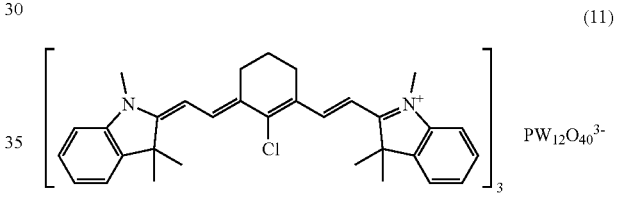

(11)

(Synthesis of Color Material Compound of Comparative Example 7)

Synthesis Example 12

A glass flask, equipped with a stirrer, a thermometer, a cooling tube, and a dropping device was charged with the following compound Basic Blue 7 (manufactured by Tokyo Chemical Industry Co., Ltd., 5.00 g) and pure water (300 g), followed by stirring at 40° C. for 30 minutes for dissolution.

[Chem. 25]

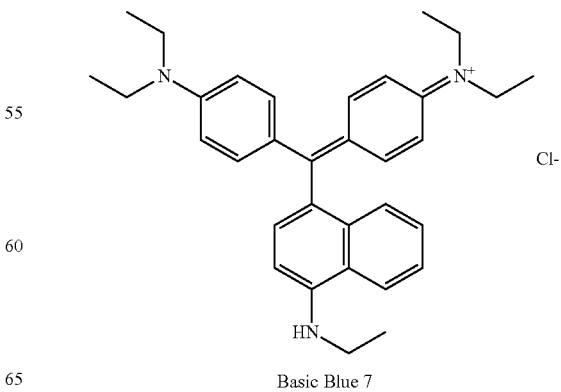

Basic Blue 7

Subsequently, a solution prepared by dissolving sodium 12-tungsto(VI)phosphate n-hydrate (manufactured by FUJI-FILM Wako Pure Chemical Corporation, 12.52 g) in pure water (60 g) was dropwise added over 2 minutes with the dropping device. After completion of the dropwise addition, stirring was performed at 40° C. for 60 minutes, the temperature was then raised to 80° C. over 30 minutes, and stirring was further performed for 90 minutes for insolubilization. Subsequently, after cooling to room temperature, filtration was performed. The solid collected by filtration was peptized with pure water (250 mL), followed by stirring for 60 minutes. After stirring, filtration was performed again, followed by washing with 200 mL of pure water. The resulting solid was dried at 90° C. for 16 hours to obtain compound 12 (14.57 g) represented by the following formula (12).

(3.4 g) was dropwise added over 15 minutes, and triethylamine (6.9 g) was then added thereto. After stirring at room temperature for 15 hours, the reaction mixture was concentrated, methanol (30 mL) was added thereto, and concentration was performed again to reduce the volume to about half. Furthermore, methanol (40 mL) and acetic acid (16 g) were added, followed by stirring for 30 minutes. The reaction product was then poured in pure water (75 mL), and the precipitate was separated. The resulting solid was dissolved in methanol (60 mL) again, followed by pouring in 50 mL of pure water. The resulting solid was washed with 50% methanol aqueous solution (40 mL) and then with pure water (30 mL), followed by drying under reduced pressure to obtain compound 13 (2.27 g) represented by the following formula (13).

[Chem. 26]

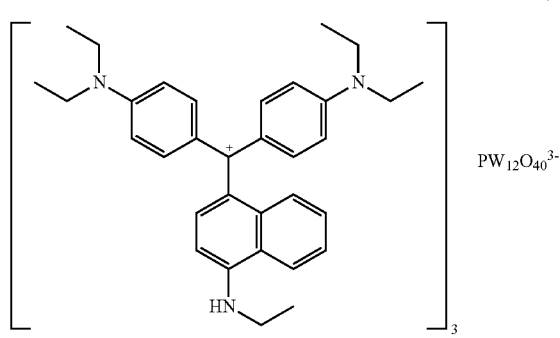

(12)

[Chem. 28]

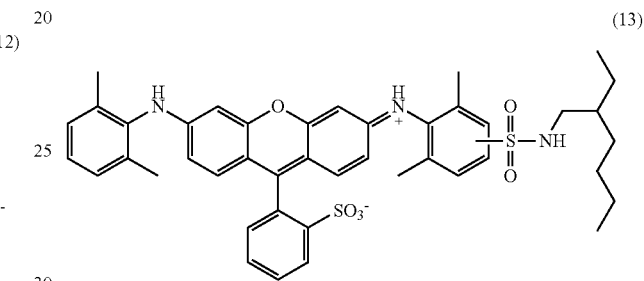

(13)

(Preparation of Toning Colored Resin Composition)

Preparation Example 3

(Synthesis of Toning Color Material)

Synthesis Example 13

A glass flask equipped with a stirrer, a thermometer, a cooling tube, and a dropping device was charged with chloroform (41 g) and dimethylformamide (2.8 g) and was kept warm at 10° C. and stirred. Thionyl chloride (3.7 g) was dropwise added to the flask, followed by stirring at 10° C. for 30 minutes. The following compound Acid Red 289 (manufactured by Tokyo Chemical Industry Co., Ltd., 5.7 g) was further added thereto. After raising the temperature to 35° C., stirring was performed for 3 hours for dissolution.

FASTOGEN (registered trademark) BLUE A540 (C.I. Pigment Blue 15:6, manufactured by DIC Corporation, 1.98 g) was dispersed with a paint conditioner (manufactured by Toyo Seiki Seisaku-sho, Ltd.) together with propylene glycol monomethyl ether acetate (manufactured by Daicel Corporation, 9.79 g), BYK (registered trademark)-LPN 21116 (manufactured by BYK-Chemie, 3.13 g), and SEPR beads of 0.3-0.4 mm in diameter (manufactured by Saint-Gobain SA, 34.2 g) for 4 hours to obtain a toning pigment dispersion (TD1).

LUXYDIR (registered trademark) ZL-295 (1.02 g) and propylene glycol monomethyl ether acetate (0.48 g) were added to and mixed with this toning pigment dispersion (TD1, 2.00 g) to obtain a toning colored resin composition (TB1) for forming a blue pixel portion fox a color filter.

(Preparation of Toning Colored Resin Composition)

Preparation Example 4

[Chem. 27]

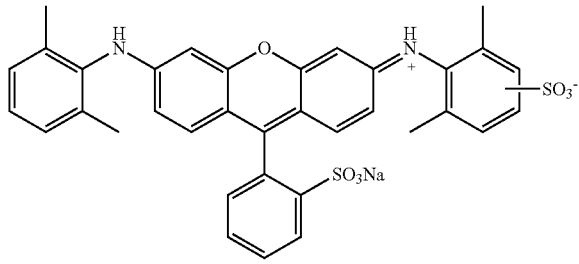

Acid Red 289

The compound 13 (0.15 g) prepared in Synthesis Example 13, cyclohexanone (manufactured by FUJIFILM Wako Pure Chemical Corporation, 3.75 g), and LUXYDIR (registered trademark) ZL-295 (3.75 g) were mixed to obtain a toning colored resin composition (TV1) for forming a blue pixel portion for a color filter.

(Preparation of Testing Colored Resin Composition)

Example 1

Subsequently, thionyl chloride (0.41 g) was added, followed by further stirring at 35° C. for 90 minutes. After decreasing the temperature to 10° C., 2-ethylhexylamine The compound 1 (1.80 g) was dispersed with a paint conditioner (manufactured by Toyo Seiki. Seisaku-sho, Ltd.) together with propylene glycol monomethyl ether acetate (11.10 g), Disperbyk (registered trademark) 2164 (manufactured by BYK-Chemie, 2.10 g), and SEPR beads of 0.3-0.4 mm in diameter (34.2 g) for 4 hours to obtain a pigment dispersion (MB1).

LUXYDIR (registered trademark) ZL-295 (1.85 g) and propylene glycol monomethyl ether acetate (0.80 g) were added to and mixed with this pigment dispersion (MB1, 3.00 g) to obtain a testing colored resin composition (PM1) for forming a blue pixel portion for a color filter.

(Preparation of Testing Colored Resin Composition)

Examples 2 to 8

Testing colored resin compositions (PM2) to (PM8) were prepared as in Example 1 except that compounds 2 to 8 were respectively used instead of compound 1.

(Preparation of Testing Colored Resin Composition)

Comparative Examples 1 to 3

Testing colored resin compositions (PM9) to (PM11) were prepared as in Example 1 except that NK-10374, NK-10739, and NK-10759 (all of them manufactured by Hayashibara Co., Ltd.) were respectively used instead of compound 1.

Examples, glass substrates (SF1) to (SF15) for single color evaluation were produced such that the colored films each have a thickness of 1.0 μm. The thickness was measured with a white-light interference microscope (VS1330) manufactured by Hitachi High-Tech Corporation.

Incidentally, the concentrations of the color material compounds in these colored films were all 26.6 mass %.

(Measurement of Absorption Spectrum of Glass Substrate for Single Color Evaluation)

Regarding each of the glass substrates (SF1) to (SF15) for single color evaluation, the absorption spectrum of the colored film was measured using a spectrophotometer (U-3900) manufactured by Hitachi High-Tech Corporation.

Figure 2:
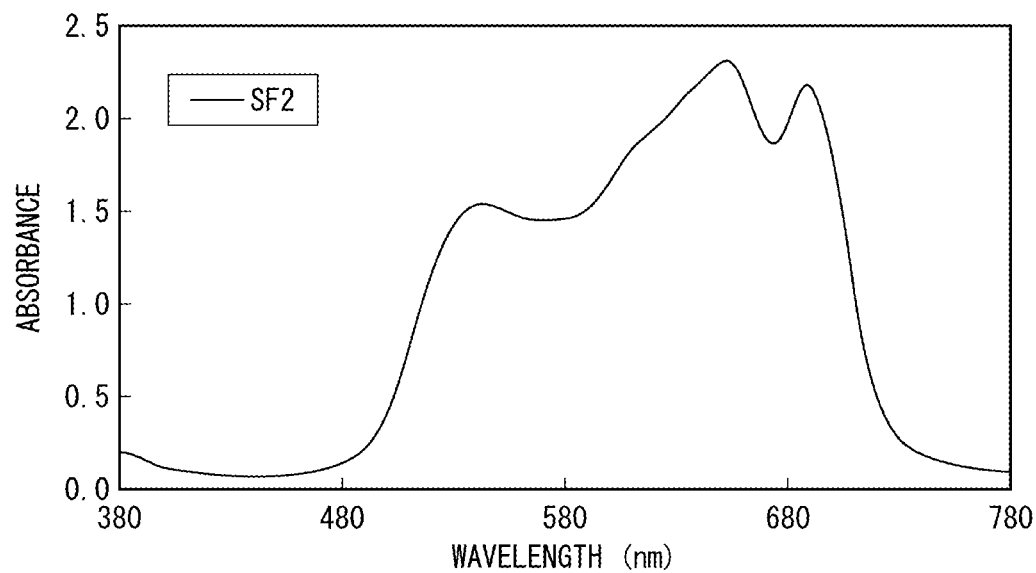
FIG. 2 is an absorption spectrum of a colored film of a glass substrate (SF2) for single color evaluation.
Figure 3:
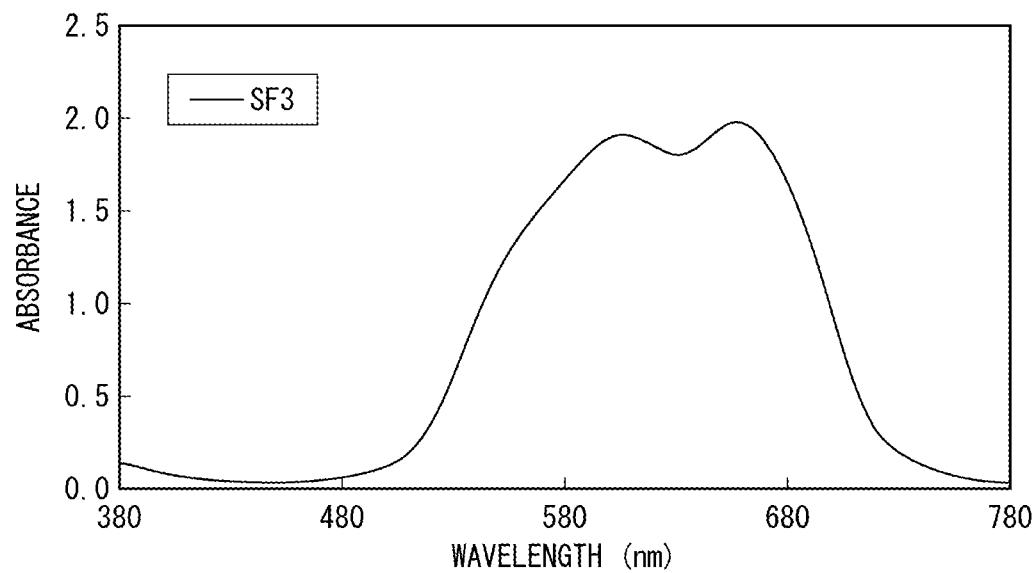
FIG. 3 is an absorption spectrum of a colored film of a glass substrate (SF3) for single color evaluation.
Figure 4:
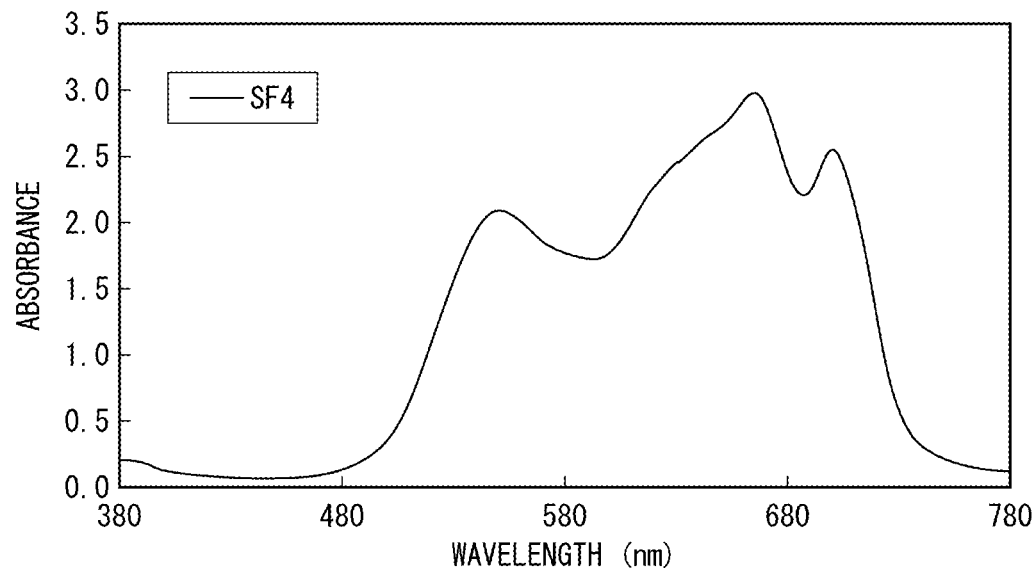
FIG. 4 is an absorption spectrum of a colored film of a glass substrate (SF4) for single color evaluation.
Figure 5:
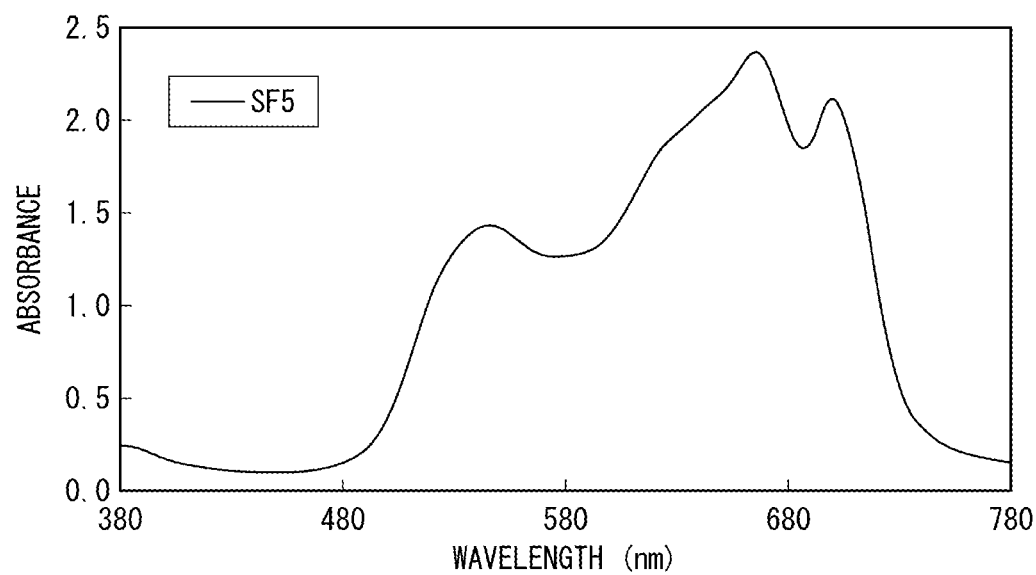
FIG. 5 is an absorption spectrum of a colored film of a glass substrate (SF5) for single color evaluation.
Figure 6:
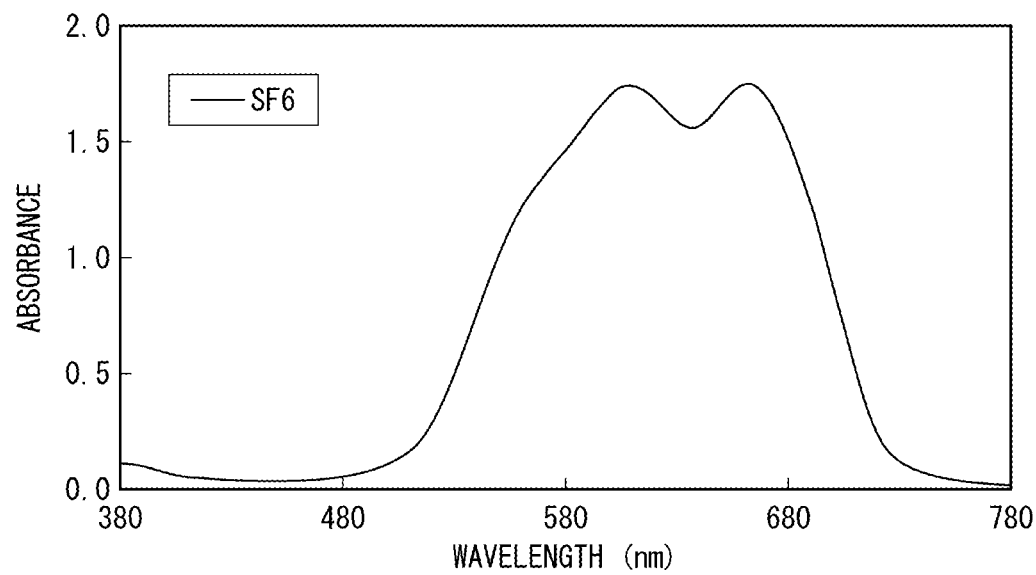
FIG. 6 is an absorption spectrum of a colored film of a glass substrate (SF6) for single color evaluation.
Figure 7:
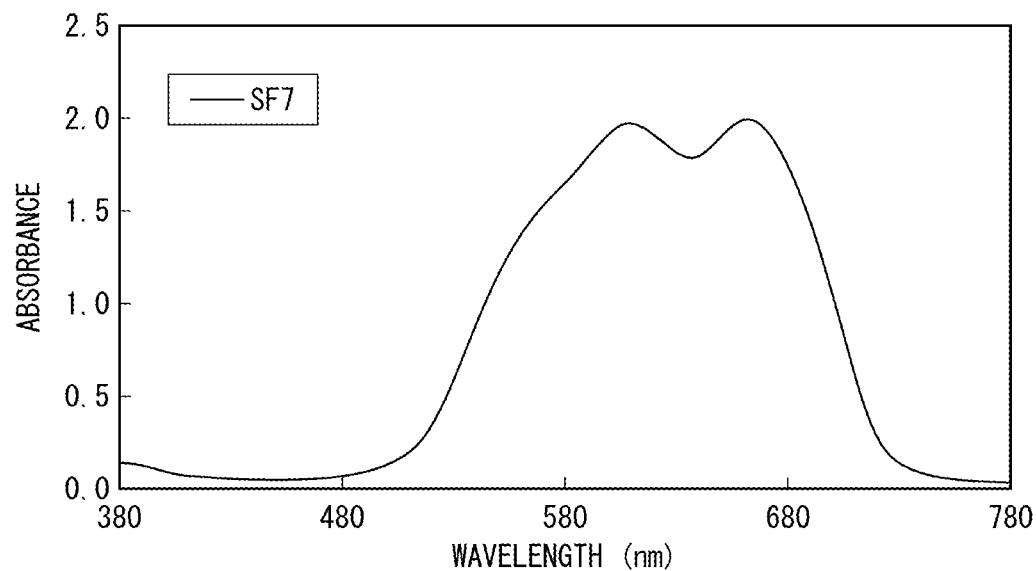
FIG. 7 is an absorption spectrum of a colored film of a glass substrate (SF7) for single color evaluation.
Figure 8:
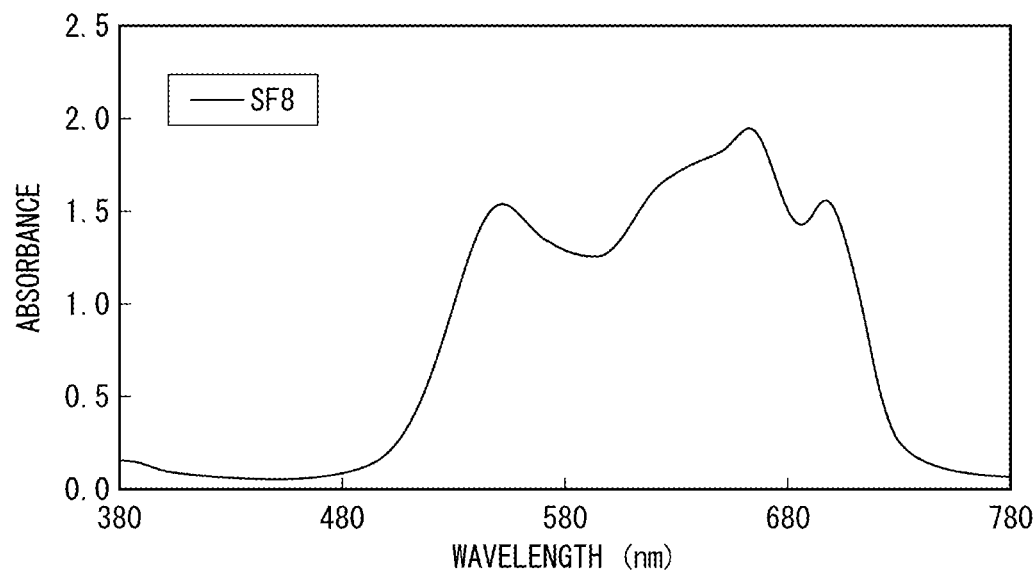
FIG. 8 is an absorption spectrum of a colored film of a glass substrate (SF8) for single color evaluation.
Figure 9:
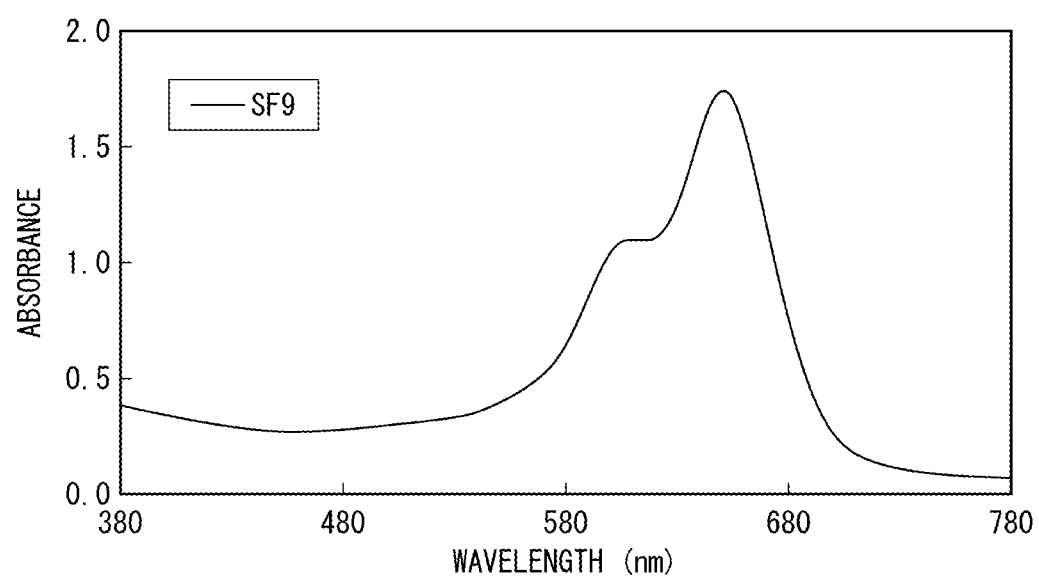
FIG. 9 is an absorption spectrum of a colored film of a glass substrate (SF9) for single color evaluation.

FIGS. 1 to 8 show the absorption spectra of colored films of glass substrates (SF1) to (SE9) for single color evaluation.

Table 1 collectively shows the following four values that are obtained from the respective absorption spectra of glass substrates (SF1) to (SF15) for single color evaluation:

(1) absorbance $A_{480}$ at wavelength 480 nm;
(2) absorbance $A_{550}$ at wavelength 550 nm;
(3) maximum absorption wavelength $\lambda_x$ on the shortest wavelength side in the wavelength range of 480 to 730 nm; and
(4) absorbance $A_x$ at $\lambda_x$.

TABLE 1

| | Color material compound | Glass substrate for single color evaluation | $A_{480}$ | $A_{550}$ | $\lambda_x$ (nm) | $A_x$ |
|---|---|---|---|---|---|---|
| Example 1 | Compound 1 | SF1 | 0.17 | 1.97 | 552 | 1.97 |
| Example 2 | Compound 2 | SF2 | 0.14 | 1.52 | 543 | 1.54 |
| Example 3 | Compound 3 | SF3 | 0.07 | 1.17 | 606 | 1.91 |
| Example 4 | Compound 4 | SF4 | 0.13 | 2.09 | 551 | 2.09 |
| Example 5 | Compound 5 | SF5 | 0.14 | 1.42 | 546 | 1.43 |
| Example 6 | Compound 6 | SF6 | 0.06 | 1.02 | 609 | 1.74 |
| Example 7 | Compound 7 | SF7 | 0.07 | 1.15 | 609 | 1.96 |
| Example 8 | Compound 8 | SF8 | 0.09 | 1.54 | 552 | 1.54 |
| Comparative Example 1 | NK-10374 | SF9 | 0.28 | 0.39 | 610 | 1.10 |
| Comparative Example 2 | NK-10739 | SF10 | 0.34 | 0.58 | 558 | 0.60 |
| Comparative Example 3 | NK-10759 | SF11 | 0.26 | 0.23 | 602 | 0.19 |
| Comparative Example 4 | Compound 9 | SF12 | 0.09 | 0.71 | 665 | 2.21 |
| Comparative Example 5 | Compound 10 | SF13 | 0.76 | 1.86 | 524 | 1.82 |
| Comparative Example 6 | Compound 11 | SF14 | 0.12 | 0.08 | N.D. | N.D. |
| Comparative Example 7 | Compound 12 | SF15 | 0.07 | 0.66 | 625 | 1.04 |

(Preparation of Testing Colored Resin Composition)

Comparative Examples 4 to 7

Testing colored resin compositions (PM12) to (PM15) were prepared as in Example 1 except that compounds 9 to 12 were respectively used instead of compound 1.

(Production of Glass Substrate for Single Color Evaluation)

Testing colored resin compositions (PM1) to (PM15) were respectively spin coated on soda glass substrates and were dried at 90° C. for 3 minutes and then heated at 230° C. for 1 hour. Consequently, glass substrates for single color evaluation each including a colored film on a soda glass substrate were produced. Incidentally, the thickness of the colored film obtained by heating at 230° C. for 1 hour was adjusted by controlling the number of spin rotation during the spin coating, and in Examples and Comparative In Comparative Example 6, N.D. means that there was no maximum absorption in the wavelength range of 480 to 780 nm.

(Preparation of Colored Resin Composition for Toning Evaluation)

The Testing colored resin compositions (PM1) to (PM15) prepared above were each blended with the toning colored resin composition (TB1) or (TV1) to prepare colored resin compositions (CR1) to (CR15) for toning evaluation for evaluating the performance as a blue pixel portion for a color filter.

The blending ratio of the blending colored resin composition (PM) and the toning colored resin composition (TB1 or TV1) was adjusted to obtain a blue pixel portion where the chromaticity (x, y) in the C light source was (0.138, 0.090).

Incidentally, which of TB1 and TV1 should be selected as the toning colored resin composition was determined by whether the hue of the blending colored resin composition (PM) is more greenish or reddish with respect to the chromaticity (0.138, 0.090). That is, toning was performed using the toning colored resin composition (TV1) when the hue of the blending colored resin composition (PM) is more greenish with respect to the chromaticity (0.138, 0.090) and using the toning colored resin composition (TB1) when the hue was more reddish. The respective colored resin compositions for toning evaluation were prepared using the toning colored resin compositions shown in Table 2.

(Production of Glass Substrate for Toning Evaluation)

The colored resin compositions (CR1) to (CR15) for evaluation were respectively spin-coated on soda glass substrates and were dried at 90° C. for 3 minutes and then heated at 230° C. for 1 hour. Consequently, glass substrates for toning evaluation each including a colored film on a soda glass substrate were produced. Incidentally, the thickness of the colored film obtained by heating at 230° C. for 1 hour was adjusted by controlling the number of spin rotation during the spin coating, and in Examples and Comparative Examples, glass substrates (CF1) to (CF15) for toning evaluation were produced such that the chromaticity (x, y) of each colored film in a C light source was (0.138, 0.090). The chromaticity (x, y) was measured with a spectrophotometer (U-3900) manufactured by Hitachi High-Tech Corporation.

(Toning Evaluation)

Regarding each of the glass substrates (CF1) to (CF15) for toning evaluation, the luminance of the colored film in a C light source, i.e., the luminance Y at a chromaticity (x, y) of (0.1380, 0.0900) was measured with a spectrophotometer (U-3900) manufactured by Hitachi High-Tech Corporation. Here, the luminance Y is a Y component of the tristimulus values of the CIE 1931 color system and is standardized so that the luminance Y is 100 in the case of full transmission. The higher the luminance Y, the better.

The results are shown in Table 2.

TABLE 2

| | Color material compound | Glass substrate for toning evaluation | Colored resin composition for toning | Luminance Y |
|---|---|---|---|---|
| Example 1 | Compound 1 | CF1 | TB1 | 8.28 |
| Example 2 | Compound 2 | CF2 | TB1 | 8.27 |
| Example 3 | Compound 3 | CF3 | TV1 | 7.96 |
| Example 4 | Compound 4 | CF4 | TB1 | 8.50 |
| Example 5 | Compound 5 | CF5 | TB1 | 7.77 |
| Example 6 | Compound 6 | CF6 | TV1 | 7.93 |
| Example 7 | Compound 7 | CF7 | TV1 | 7.89 |
| Example 8 | Compound 8 | CF8 | TV1 | 8.11 |
| Comparative Example 1 | NK-10374 | CF9 | — | Impossible to tone |
| Comparative Example 2 | NK-10739 | CF10 | — | Impossible to tone |
| Comparative Example 3 | NK-10759 | CF11 | — | Impossible to tone |
| Comparative Example 4 | Compound 9 | CF12 | TV1 | 6.44 |
| Comparative Example 5 | Compound 10 | CF13 | TB1 | 7.33 |
| Comparative Example 6 | Compound 11 | CF14 | — | Impossible to tone |
| Comparative Example 7 | Compound 12 | CF15 | TV1 | 7.06 |

In color material compounds of Comparative Examples 1 to 3 and 6, no blue pixel portion having a chromaticity (x, y) of (0.138, 0.090) was obtained by using any of the toning colored resin compositions TB1 and TV1. That is, it can be said that the color material compounds of Comparative Examples 1 to 3 and 6 are not suitable for a blue pixel portion.

As shown in Table 2, the colored films formed using the compounds of Examples 1 to 8 showed higher luminance Y than the colored films formed using the color material compounds of: Comparative Examples 4, 5, and 7. The compounds of Examples 1 to 8 are excellent as color material compounds constituting a blue pixel portion of a color filter.

INDUSTRIAL APPLICABILITY

The compound of the present invention can be suitably used for forming a blue pixel portion of a color filter.

What is claimed is:

1. A compound represented by following general formula (I):

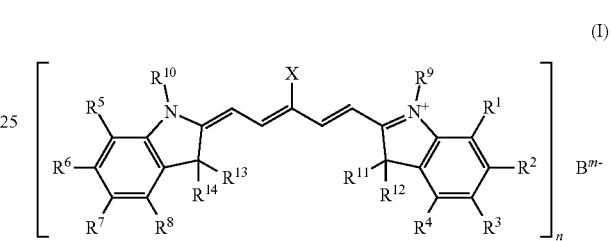

in formula (I),
X represents a methyl group or a halogen atom;
$R^1$ to $R^{14}$ each independently represent a hydrogen atom, a halogen atom, a cyano group, a nitro group, an optionally N-alkylated amino group or ammonium group, a hydroxy group, an allyloxy group, an alkoxy group, a sulfo group, an optionally N-alkylated sulfamoyl group, a carboxyl group, an ester group, an optionally N-alkylated amide group, an optionally substituted hydrocarbon group having 1 to 12 carbon atoms, an optionally substituted aromatic hydrocarbon group having 6 to 12 carbon atoms, or an optionally substituted heterocyclic group having 3 to 12 carbon atoms, or adjacent two selected from $R^1$ to $R^4$, adjacent two selected from $R^5$ to $R^8$, $R^{11}$ and $R^{12}$, or $R^{13}$ and $R^{14}$ are bonded to each other to form a ring;
$B^{m-}$ represents a polyoxometalate anion comprising tungsten;
m represents an integer of 1 to 20; and
n represents an integer of 1 to 20,
provided that n is determined such that the charge of the whole formula (I) becomes zero.

2. The compound according to claim 1, wherein in the formula (I), X is a methyl group, a chlorine atom, or a bromine atom.

3. The compound according to claim 1, wherein in the formula (I), $B^{m-}$ is $(PW_{12}O_{40})^{3-}$, $(PMoW_{11}O_{40})^{3-}$, $(SiW_{12}O_{40})^{4-}$, or $(SiMoW_{11}O_{40})^{4-}$.

4. The compound according to claim 1, wherein in the formula (I), X is a methyl group, a chlorine atom, or a bromine atom.

5. The compound according to claim 3, wherein in the formula (I), X is a methyl group, a chlorine atom, or a bromine atom.

* * * * *